(12) United States Patent
Huston et al.

(10) Patent No.: US 11,207,518 B2
(45) Date of Patent: Dec. 28, 2021

(54) TREATING INFLAMMATORY DISORDERS BY STIMULATION OF THE CHOLINERGIC ANTI-INFLAMMATORY PATHWAY

(75) Inventors: Jared M. Huston, New York, NY (US); Kevin J. Tracey, Old Greenwich, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 462 days.

(21) Appl. No.: 12/259,208

(22) Filed: Oct. 27, 2008

(65) Prior Publication Data
US 2009/0143831 A1    Jun. 4, 2009

Related U.S. Application Data

(63) Continuation-in-part of application No. 11/318,075, filed on Dec. 22, 2005.

(60) Provisional application No. 60/639,332, filed on Dec. 27, 2004, provisional application No. 60/982,681, filed on Oct. 25, 2007.

(51) Int. Cl.
*A61N 1/05* (2006.01)
*A61N 1/36* (2006.01)

(52) U.S. Cl.
CPC ..... *A61N 1/36053* (2013.01); *A61N 1/36171* (2013.01); *A61N 1/36114* (2013.01); *A61N 1/36153* (2013.01)

(58) Field of Classification Search
CPC ......... A61N 1/0551; A61N 1/056; A61N 1/05
USPC ............................... 607/2, 3, 39, 42, 45, 48
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |

(Continued)

FOREIGN PATENT DOCUMENTS

| | | |
|---|---|---|
| CN | 201230913 | 5/2009 |
| CN | 101528303 A | 9/2009 |

(Continued)

OTHER PUBLICATIONS

US 6,184,239 B1, 02/2001, Puskas (withdrawn)

(Continued)

*Primary Examiner* — Michael J D Abreu
(74) *Attorney, Agent, or Firm* — Shay Glenn LLP

(57) ABSTRACT

Described herein are methods for treating a subject suffering from or at risk for a condition mediated by an inflammatory cytokine cascade, by electrically or mechanically stimulating vagus nerve activity in an amount sufficient to inhibit the inflammatory cytokine cascade.

17 Claims, 11 Drawing Sheets

(56) References Cited

U.S. PATENT DOCUMENTS

| | | |
|---|---|---|
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A * | 7/1996 | Terry et al. ............ 607/40 |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |

(56) References Cited

U.S. PATENT DOCUMENTS

| | | |
|---|---|---|
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 * | 1/2007 | Knudson ............ A61N 1/05 607/133 |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,855,767 B2 | 10/2014 | Faltys et al. |
| 9,662,490 B2 | 5/2017 | Tracey et al. |
| 9,700,716 B2 | 7/2017 | Faltys et al. |
| 9,849,286 B2 | 12/2017 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 * | 12/2003 | Whitehurst et al. ............ 607/39 |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 * | 10/2004 | Tracey et al. .................. 514/12 |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |

(56) References Cited

U.S. PATENT DOCUMENTS

| | | |
|---|---|---|
| 2005/0007570 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0125044 A1 | 6/2005 | Tracey et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1* | 7/2005 | Boveja et al. .................. 607/45 |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0282906 A1 | 12/2005 | Tracey et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |

(56) References Cited

U.S. PATENT DOCUMENTS

| | | |
|---|---|---|
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125079 A1 | 5/2009 | Armstrong et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0254143 A1 | 10/2009 | Tweden et al. |
| 2009/0276019 A1 | 11/2009 | Perez et al. |
| 2009/0281593 A9 * | 11/2009 | Errico et al. .................. 607/42 |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0125304 A1 | 5/2010 | Faltys |
| 2010/0215632 A1 | 8/2010 | Boss et al. |
| 2010/0241183 A1 | 9/2010 | DiLorenzo |
| 2010/0249859 A1 | 9/2010 | DiLorenzo |
| 2010/0280569 A1 | 11/2010 | Bobillier et al. |
| 2011/0004266 A1 | 1/2011 | Sharma |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0224749 A1 | 9/2011 | Ben-David et al. |
| 2011/0275927 A1 | 11/2011 | Wagner et al. |
| 2012/0065706 A1 | 3/2012 | Vallapureddy et al. |
| 2012/0179219 A1 | 7/2012 | Kisker et al. |
| 2013/0317580 A1 | 11/2013 | Simon et al. |
| 2014/0046407 A1 | 2/2014 | Ben-Ezra et al. |
| 2014/0330349 A1 | 11/2014 | Levine et al. |
| 2015/0057722 A1 | 2/2015 | Faltys et al. |
| 2015/0066123 A1 | 3/2015 | Faltys et al. |
| 2016/0038745 A1 | 2/2016 | Faltys et al. |
| 2016/0067497 A1 | 3/2016 | Levine et al. |
| 2016/0114165 A1 | 4/2016 | Levine et al. |
| 2016/0331952 A1 | 11/2016 | Faltys et al. |
| 2017/0113044 A1 | 4/2017 | Levine et al. |
| 2017/0197076 A1 | 7/2017 | Faltys et al. |
| 2017/0202467 A1 | 7/2017 | Zitnik et al. |
| 2017/0203103 A1 | 7/2017 | Levine et al. |
| 2017/0209705 A1 | 7/2017 | Faltys et al. |
| 2017/0266448 A1 | 9/2017 | Tracey et al. |
| 2017/0304613 A1 | 10/2017 | Faltys et al. |
| 2018/0001096 A1 | 1/2018 | Faltys et al. |
| 2018/0117320 A1 | 5/2018 | Levine et al. |
| 2019/0046799 A1 | 2/2019 | Levine et al. |
| 2019/0111263 A1 | 4/2019 | Levine et al. |
| 2019/0117979 A1 | 4/2019 | Tracey et al. |
| 2019/0366078 A1 | 12/2019 | Faltys et al. |
| 2020/0206515 A1 | 7/2020 | Faltys et al. |
| 2020/0330760 A1 | 10/2020 | Levine et al. |

FOREIGN PATENT DOCUMENTS

| | | |
|---|---|---|
| CN | 101578067 A | 11/2009 |
| CN | 101868280 A | 10/2010 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| KR | 20050039445 A | 4/2005 |
| WO | WO1993/001862 A1 | 2/1993 |
| WO | WO1997/030998 A1 | 8/1997 |
| WO | WO1998/020868 A1 | 5/1998 |
| WO | WO2000/027381 A2 | 5/2000 |
| WO | WO2000/047104 A2 | 8/2000 |
| WO | WO2001/000273 A1 | 1/2001 |
| WO | WO2001/008617 A1 | 2/2001 |
| WO | WO2001/089526 A1 | 11/2001 |
| WO | WO2002/044176 A1 | 6/2002 |
| WO | WO2002/057275 A1 | 7/2002 |
| WO | WO2003/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO 2007/133718 A2 | 11/2007 |
| WO | WO2010/005482 A1 | 1/2010 |

OTHER PUBLICATIONS

Faltys et al.; U.S. Appl. No. 12/917,197 entitled "Modulation of the cholinergic anti-inflammatory pathway to treat pain or addiction," filed Nov. 1, 2010.

Faltys et al.; U.S. Appl. No. 12/978,250 entitled "Neural stimulation devices and systems for treatment of chronic inflammation," filed Dec. 23, 2010.

Ben-Noun et al.; Neck circumference as a simple screening measure for identifying overweight and obese patients; Obesity Research; vol. 9; No. 8; pp. 470-477; Aug. 8, 2001.

Bushby et al.; Centiles for adult head circumference; Archives of Disease in Childhood; vol. 67; pp. 1286-1287; 1992.

Hansson, E.; Could chronic pain and spread of pain sensation be induced and maintained by glial activation?. Acta Physiologica, vol. 187: p. 321R327, 2006.

Pulvirenti et al.; Drug dependence as a disorder of neural plasticity:focus on dopamine and glutamate; Rev Neurosci.; vol. 12; No. 2; pp. 141-158; 2001.

Suter et al.; Do glial cells control pain?; Neuron Glia Biol.; vol. 3; No. 3; pp. 255-268; Aug. 2007.

Saghizadeh et al.; The expression of TNF? by human muscle; J. Clin. Invest.; vol. 97; No. 4; pp. 1111-1116; 1996.

Payne, J. B et al., Nicotine effects on PGE2 and IL-1 beta release by LPS-treated human monocytes, J. Perio. Res., vol. 31, No. 2, pp. 99-104, 1996.

(56) References Cited

OTHER PUBLICATIONS

Pullan, R. D., et al., Transdermal nicotine for active ulceratiive colitis, N. Engl. J. Med., vol. 330, No. 12, pp. 811-815, 1994.
Takeuchi et al., A comparision between Chinese blended medicine "Shoseiryuto" tranilast and ketotifen on the anit-allergic action in the guinea pigs, Allergy, vol. 34, No. 6, pp. 387-393, 1985 (eng. abstract).
Benthem et al.; Parasympathetic inhibition of sympathetic neural activity to the pancreas; Am.J.Physiol Endocrinol.Metab; 280; pp. E378-E381; 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Besedovsky, H., et al., Immunoregulatory feedback between interleukin-1 and glucocorticoid hormones, Science, vol. 233, pp. 652-654, 1986.
Blackwell, T. S. et al., Sepsis and cytokines: current status, Br. J. Anaesth., vol. 77, pp. 110-117, 1996.
Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.
Bulloch et al.; Characterization of choline O-acetyltransferase (ChAT) in the BALB/C mouse spleen; Int.J.Neurosci.; 76; pp. 141-149; 1994.
Burke et al., Bent pseudoknots and novel RNA inhibitors of type 1 human immunodeficiency virus (HIV-1) reverse transcriptase, J. Mol. Biol., vol. 264; pp. 650-666, 1996.
Cano et al.; Characterization of the central nervous system innervation of the rat spleen using viral transneuronal tracing; J.Comp Neurol.; 439; pp. 1-18; 2001.
Das, Critical advances in spticemia and septic shock, Critical Care, vol. 4, pp. 290-296, Sep. 7, 2000.
Del Signore et al.; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Ellington et al., In vitro selection of RNA molecules that bind specific ligands, Nature, vol. 346, pp. 818-822, Aug. 30, 1990.
Fox, D. A., Cytokine blockade as a new strategy to treat rheumatoid arthritis, Arch. Intern. Med., vol. 160, pp. 437-444, Feb. 28, 2000.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, 1995.
Ghelardini et al., S-(−)-ET 126: A potent and selective M1 antagonist in vitro and in vivo, Life Sciences, vol. 58, No. 12, pp. 991-1000, 1996.
Goyal et al.. Nature of the vagal inhibitory innervation to the lower esophageal sphincter, Journal of Clinical Investigation, vol. 55, pp. 1119-1126, May 1975.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Guslandi, M., Nicotine treatment for ulcerative colitis, Br. J. Clin. Pharmacol., vol. 48, pp. 481-484, 1999.
Harrison's Principles of Internal Medicine, vol. 13, pp. 511-515 and 1433-1435, 1994.
Hirao et al., the limits of specificity: an experimental analysis with RNA aptamers to MS2 coat protein variants, Mol. Divers., vol. 4, pp. 75-89, 1999.
Hsu, et al., Analysis of efficiency of magnetic stimulation, IEEE Trans. Biomed. Eng., vol. 50(11), pp. 1276-1285, Nov. 2003.

Jaeger et al., The structure of HIV-1 reverse transcriptase complexed with an RNA pseudoknot inhibitor, The EMBO Journal, 17(15), pp. 4535-4542, 1998.
Joshi et al., Potent inhibition of human immunodeficiency virus type 1 replection by template analog reverse transcriptase , J. Virol., 76(13), pp. 6545-6557, Jul. 2002.
Kawashima, et al., Extraneuronal cholinergic system in lymphocytes, Pharmacology & Therapeutics, vol. 86, pp. 29-48, 2000.
Kees et al.; Via beta-adrenoceptors, stimulation of extrasplenic sympathetic nerve fibers inhibits lipopolysaccharide-induced TNF secretion in perfused rat spleen; J.Neuroimmunol.; 145; pp. 77-85; 2003.
Kensch et al., HIV-1 reverse transcriptase-pseudoknot RNA aptamer interaction has a binding affinity in the low picomolar range coupled with high specificity, J. Biol. Chem., 275(24), p. 18271-18278, Jun. 16, 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
LeNovere, N. et al., Molecular evolution of the nicotinic acetylcholine receptor: an example of multigene family in excitable cells, J. Mol. Evol., 40, pp. 155-172, 1995.
Leonard, S. et al., Neuronal nicotinic receptors: from structure to function, Nicotine & Tobacco Res. 3:203-223 (2001).
Lips et al.; Coexpression and spatial association of nicotinic acetylcholine receptor subunits alpha7 and alpha10 in rat sympathetic neurons; J.Mol.Neurosci.; 30; pp. 15-16; 2006.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, 1996.
Nagashima et al., Thrombin-activatable fibrinolysis inhibitor (TAFI) deficiency is compatible with murine life, J. Clin. Invest., 109, pp. 101-110, 2002.
Noguchi et al., Increases in Gastric acidity in response to electroacupuncture stimulation of hindlimb of anesthetized rats, Jpn. J. Physiol., 46(1), pp. 53-58, 1996.
Norton, Can ultrasound be used to stimulate nerve tissue, BioMedical Engineering, 2(1), pp. 6, 2003.
Rinner et al.; Rat lymphocytes produce and secrete acetylcholine in dependence of differentiation and activation; J.Neuroimmunol.; 81; pp. 31-37; 1998.
Saindon et al.; Effect of cervical vagotomy on sympathetic nerve responses to peripheral interleukin-1 beta; Auton.Neuroscience Basic and Clinical; 87; pp. 243-248; 2001.
Saito, Involvement of muscarinic M1 receptor in the central pathway of the serotonin-induced bezold-jarisch reflex in rats, J. Autonomic Nervous System, vol. 49, pp. 61-68, 1994.
Sandborn, W. J., et al., Transdermal nicotine for mildly to moderately active ulcerative colitis, Ann. Intern. Med, vol. 126, No. 5, pp. 364-371, 1997.
Sato, E., et al., Acetylcholine stimulates alveolar macrophages to release inflammatory cell chemotactic activity, Am. J. Physiol., vol. 274, pp. L970-L979, 1998.
Sato, K.Z., et al. Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, 1999.
Schneider et al., High-affinity ssDNA inhibitors of the review transcriptase of type 1 human immunodeficiency virus, Biochemistry, 34(29), pp. 9599-9610, 1995.
Shafer, Genotypic testing for human immunodeficiency virus type 1 drug resistance, Clinical Microbiology Reviews, vol. 15, pp. 247-277, 2002.
Sher, M. E., et al., The influence of cigarette smoking on cytokine levels in patients with inflammatory bowel disease, Inflamm. Bowel Dis., vol. 5, No. 2, pp. 73-78, 1999.
Snyder et al., Correction of hemophilia B in canine and murine models using recombinant adeno-associated viral vectors; Nature Medicine, 5(1), pp. 64-70, Jan. 1999.
Steinlein, New functions for nicotine acetylcholine receptors?, Behavioural Brain Res., vol. 95, pp. 31-35, 1998.

(56) References Cited

OTHER PUBLICATIONS

Sternberg, E. M., Perspectives series: cytokines and the brain 'neural-immune interactions in health and disease,' J. Clin. Invest., vol. 100, No. 22, pp. 2641-2647, Dec. 1997.
Sykes, et al., An investigation into the effect and mechanisms of action of nicotine in inflammatory bowel disease, Inflamm. Res., vol. 49, pp. 311-319, 2000.
Toyabe, et al., Identification of nicotinic acetylcholine receptors on lymphocytes in the periphery as well as thymus in mice, Immunology, vol. 92, pp. 201-205, 1997.
Tracey, K. J. et al., Anti-cachectin/TNF monoclonal antibodies prevent septic shock during lethal bacteraemia; Nature, 330: pp. 662-664, 1987.
Tsutsui, H., et al., Pathophysiolocical roles of interleukin-18 in inflammatory liver diseases; Immunol. Rev., 174:192-209, 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, 1998.
Walland et al., Compensation of muscarinic brochial effects of talsaclidine by concomitant sympathetic activation in guinea pigs; European Journal of Pharmacology, vol. 330, pp. 213-219, 1997.
Wang et al.; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183, pp. 27-31, 1995.
Webster's Dictionary, definition of "intrathecal", online version accessed Apr. 21, 2009.
Whaley, K. et al., C2 synthesis by human monocytes is modulated by a nicotinic cholinergic receptor, Nature, vol. 293, pp. 580-582, Oct. 15, 1981.
Tracey et al.; U.S. Appl. No. 12/415,671 entitled "Methods and systems for reducing inflammation by neuromodulation of T-cell activity," filed Mar. 31, 2009.
Faltys et al.; U.S. Appl. No. 12/434,462 entitled "Vagus nerve stimulation electrodes and methods of use," filed May 1, 2009.
Cicala et al., "Linkage between inflammation and coagulation: An update on the molecular basis of the crosstalk," Life Sciences, vol. 62(20); pp. 1817-1824, 1998.
Kalishevskaya et al. "The character of vagotomy-and atropin-induced hypercoagulation," Fizio. Zh SSSR Im I M Sechenova, 65(3): pp. 398-404, 1979.
Khatun, S., et al., "Induction of hypercoagulability condition by chronic localized cold stress in rabbits," Thromb. and Haemost., 81: pp. 449-455, 1999.
Kudrjashov, et al. "Reflex nature of the physiological anticoagulating system," Nature, vol. 196(4855): pp. 647-649; 1962.
Kuznik, et al., "Secretion of blood coagulation factors into saliva under conditions of hypo-and hypercoagulation," Voprosy Meditsinskoi Khimii, vol. 19(1): pp. 54-57; 1973.
Kuznik, et al., "Heart as an efferent regulator of the process of blood coagulation and fibrinolysis," Kardiologiia, vol. 13(3): pp. 10-17, 1973.
Kuznik, et al., "Blood Coagulation in stimulation of the vagus nerve in cats," Biull. Eskp. Biol. Med., vol. 78(7): pp. 7-9, 1974.
Kuznik, et al., "The role of the vascular wall in the mechanism of control of blood coagulation and fibrinolysis on stimulation of the vagus nerve," Cor Vasa, vol. 17(2): pp. 151-158, 1975.
Kuznik, et al., "The dynamics of procoagulatible and fibrinolytic activities during electrical stimulation of peripheral nerves," Fizio. Zh SSSR Im I M Sechenova, 3: pp. 414-420, 1979.
Lang, et al., "Neurogienic control of cerebral blood flow," Experimental Neurology, 43: pp. 143-161, 1974.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Mishchenko, et al., "Coagulation of the blood and fibrinolysos in dogs during vagal stimulation," Fizio. Zh SSSR Im I M Sechenova, vol. 61(1): pp. 101-107, 1975.
Von Känal, et al., Effects of sympathetic activation by adrenergic infusions on hemostasis in vivo, Eur. J. Haematol., vol. 65: pp. 357-369, 2000.
Cohen, "The immunopathogenesis of sepsis," vol. 420(19): pp. 885-891, 2002.
Weiner, et al., "Inflammation and therapeutic vaccination in CNS diseases," vol. 420(19): pp. 879-884, 2002.
Benoist, et al., "Mast cells in autoimmune disease" vol. 420(19): pp. 875-878, 2002.
Abraham, Coagulation abnormalities in acute lung injury and sepsis, Am. J. Respir. Cell Mol. Biol., vol. 22, pp. 401-404, 2000.
Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.
Antonica, A., et al., Vagal control of lymphocyte release from rat thymus, J. Auton. Nerv. Syst., vol. 48, pp. 187-197, 1994.
Asakura et al., Non-surgical therapy for ulcerative colitis, Nippon Geka Gakkai Zasshi, vol. 98, No. 4, pp. 431-437, Apr. 1997 (abstract only).
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Bhattacharya, S.K. et al., Central muscarinic receptor subtypes and carrageenin-induced paw oedema in rats, Res. Esp. Med. Vol. 191, pp. 65-76, 1991.
Bianchi et al., Suppression of proinflammatory cytokines in monocytes by a tetravalent guanylhydrazone, Journal of Experimental Medicine, vol. 183, pp. 927-936, Mar. 1996.
Blum, A. et al., Role of cytokines in heart failure, Am. Heart J., vol. 135, pp. 181-186, 1998.
Boldyreff, Gastric and intestinal mucus, its properties and physiological importance, Acta Medica Scandinavica (journal), vol. 89, pp. 1-14, 1936.
Borovikova et al., Efferent vagus nerve activity attenuates cytokine-mediated inflammation, Society for Neuroscience Abstracts, vol. 26, No. 102, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11,1999, Molecular, cellular, and systemic pathobioigal aspects

(56) References Cited

OTHER PUBLICATIONS and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bumgardner, G. L. et al., Transplantation and cytokines, Seminars in Liver Disease, vol. 19, No. 2, pp. 189-204, 1999.
Carteron, N. L., Cytokines in rheumatoid arthritis: trials and tribulations, Mol. Med. Today, vol. 6, pp. 315-323, 2000.
Corcoran, et al., The effects of vagus nerve stimulation on pro- and anti-inflammatory cytokines in humans: a preliminary report, NeuroImmunoModulation, vol. 12, pp. 307-309, 2005.
Dibbs, Z., et al., Cytokines in heart failure: pathogenetic mechanisms and potential treatment, Proc. Assoc. Am. Physicians, vol. 111, No. 5, pp. 423-428, 1999.
Dinarello, C. A., The interleukin-1 family: 10 years of discovery, FASEB J., vol. 8, No. 15, pp. 1314-1325, 1994.
Doshi et al., Evolving role of tissue factor and its pathway inhibitor, Crit. Care Med., vol. 30, suppl. 5, pp. S241-S250, 2002.
Esmon, The protein C pathway, Crit. Care Med., vol. 28, suppl. 9, pp. S44-S48, 2000.
Fleshner, M., et al., Thermogenic and corticosterone responses to intravenous cytokines (IL-1? and TNF-?) are attenuated by subdiaphragmatic vagotomy, J. Neuroimmunol., vol. 86, pp. 134-141, 1998.
Fox, et al., Use of muscarinic agonists in the treatment of Sjorgren syndrome, Clin. Immunol., vol. 101, No. 3; pp. 249-263, 2001.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, 2000.
Ghia, et al., The vagus nerve: a tonic inhibitory influence associated with inflammatory bowel disease in a murine model, Gastroenterology, vol. 131, pp. 1122-1130, 2006.
Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, 2007.
Gracie, J. A., et al., A proinflammatory role for IL-18 in rheumatoid arthritis, J. Clin. Invest., vol. 104, No. 10, pp. 1393-1401, 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Hirano, T., Cytokine suppresive agent improves survival rate in rats with acute pancreatitis of closed duodenal loop, J. Surg. Res., vol. 81, No. 2, pp. 224-229, 1999.
Holladay et al., Neuronal nicotinic acetylcholine receptors as targets for drug discovery, Journal of Medicinal Chemistry, 40, pp. 4169-4194, 1997.
Hommes, D. W. et al., Anti- and Pro-inflammatory cytokines in the pathogenesis of tissue damage in Crohn's disease, Current Opinion in Clinical Nutrition and Metabolic Care, vol. 3., pp. 191-195, 2000.
Hsu, H. Y., et al.. Cytokine release of peripheral blood monoculear cells in children with chronic hepatitis B virus infection, J. Pediatr. Gastroenterol., vol. 29, No. 5, pp. 540-545, 1999.
Hu, et al., The effect of norepinephrine on endotoxin-mediated macrophage activation, J. Neuroimmunol., vol. 31, pp. 35-42, 1991.
Huston et al.; J. Exp. Med. 2006; vol. 203; pp. 1623-1628; 2006.
Ilton et al., "Differential expression of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.

Jander, S. et al., Interleukin-18 is induced in acute inflammatory demyelinating polymeuropathy, J. Neuroimmunol., vol. 114, pp. 253-258, 2001.
Kanai, T. et al., Interleukin-18 and Crohn's disease, Digestion, vol. 63, suppl. 1, pp. 37-42, 2001.
Katagiri, M., et al., Increased cytokine production by gastric mucosa in patients with helicobacter pylori infection, J. Clin. Gastroenterol., vol. 25, Suppl. 1, pp. S211-S214, 1997.
Kimball, et al., Levamisole causes differential cytokine expression by elicited mouse peritoneal macrophases, Journal of Leukocyte Biology, vo. 52, No. 3, pp. 349-356, 1992 (abstract only).
Kimmings, A. N., et al., Systemic inflammatory response in acute cholangitis and after subsequent treatment, Eur. J. Surg., vol. 166, pp. 700-705, 2000.
Kirchner et al.; Left vagus nerve stimulation suppresses experimentally induced pain; Neurology; vol. 55; pp. 1167-1171; 2000.
Kumins, N. H., et al., Partial hepatectomy reduces the endotoxin-induced peak circulating level of tumor necrosis factor in rats, Shock, vol. 5, No. 5, pp. 385-388, 1996.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, 1995.
Lipton, J. M et al.; Anti-inflammatory actions of the neuroimmunomodulator ?-MSH, Immunol. Today, vol. 18, pp. 140-145, 1997.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, 2000.
Minnich et al.; Anti-cytokine and anti-inflammatory therapies for the treatment of severe sepsis: progress and pitfalls; Proceedings of the Nutrition Society; vol. 63; pp. 437-441; 2004.
Molina et al., CNI-1493 attenuates hemodynamic and pro-inflammatory responses to LPS, Shock, vol. 10, No. 5, pp. 329-334, Nov. 1998.
Nathan, C. F., Secretory products of macrophages, J. Clin. Invest., vol. 79, pp. 319-326, 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; 2001.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Prystowsky, J. B. et al., Interleukin-1 mediates guinea pig gallbladder inflammation in vivo, J. Surg. Res., vol. 71, No. 2, pp. 123-126, 1997.
Pulkki, K. J., Cytokines and cardiomyocyte death, Ann. Med., vol. 29, pp. 339-343, 1997.
Rayner, S. A. et al., Local bioactive tumour necrosis factor (TNF) in corneal allotransplantation, Clin. Exp. Immunol., vol. 122, pp. 109-116, 2000.
Romanovsky, A. A., et al.,The vagus nerve in the thermoregulatory response to systemic inflammation, Am. J. Physiol., vol. 273, No. 1 (part 2), pp. R407-R413, 1997.
Scheinman, R. I., et al., Role of transcriptional activation of l?B? in mediation of immunosuppression by glucocorticoids, Science, vol. 270, pp. 283-286, 1995.
Shapiro et al.; Prospective, randomised trial of two doses of rFVIIa (NovoSeven) in haemophilia patients with inhibitors undergoing surgery; Thromb Haemost; vol. 80; pp. 773-778; 1998.
Stalcup et al., Endothelial cell functions in the hemodynamic responses to stress, Annals of the New York Academy of Sciences, vol. 401, pp. 117-131, 1982.
Sugano et al., Nicotine inhibits the production of inflammatory mediators in U937 cells through modulation of nuclear factor-

(56) References Cited

OTHER PUBLICATIONS kappaβ activation, Biochemical and Biophysical Research Communications, vol. 252, No. 1, pp. 25-28, Nov. 9, 1998.
Tracey et al., Mind over immunity, Faseb Journal, vol. 15, No. 9, pp. 1575-1576, Jul. 2001.
Tracey, K. J. et al., Shock and tissue injury induced by recombinant human cachectin, Science, vol. 234, pp. 470-474, 1986.
Tracey, K.J., The inflammatory reflex, Nature, vol. 420, pp. 853-859, 2002.
Vanhoutte, et al., Muscarinic and beta-adrenergic prejunctional modulation of adrenergic neurotransmission in the blood vessel wall, Gen Pharmac., vol. 14, pp. 35-37, 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16, pp. 101-102, 2000.
Villa et al., Protection against lethal polymicrobial sepsis by CNI-1493, an inhibitor of pro-inflammatory cytokine synthesis, Journal of Endotoxin Research, vol. 4, No. 3, pp. 197-204, 1997.
Von Känal, et al., Effects of non-specific ?-adrenergic stimulation and blockade on blood coagulation in hypertension, J. Appl. Physiol., vol. 94, pp. 1455-1459, 2003.
Waserman, S. et al., TNF-? dysregulation in asthma: relationship to ongoing corticosteroid therapy, Can. Respir. J., vol. 7, No. 3, pp. 229-237, 2000.
Watanabe, H. et al., The significance of tumor necrosis factor (TNF) levels for rejection of joint allograft, J. Reconstr. Microsurg., vol. 13, No. 3, pp. 193-197, 1997.
Watkins, L.R. et al., Implications of immune-to-brain communication for sickness and pain, Proc. Natl. Acad. Sci. U.S.A., vol. 96, pp. 7710-7713, 1999.
Woiciechowsky, C. et al., Sympathetic activation triggers systemic interleukin-10 release in immunodepression induced by brain injury, Nature Med., vol. 4, No. 7, pp. 808-813, 1998.
Yeh, S.S. et al., Geriatric cachexia: the role of cytokines, Am. J. Clin. Nutr., vol. 70, pp. 183-197, 1999.
Zhang et al., Tumor necrosis factor, The Cytokine Handbook, 3rd ed., Ed. Thompson, Academic Press, pp. 517-548, 1998.
Tracey et al.; U.S. Appl. No. 12/109,334 entitled "Inhibition of inflammatory cytokine production by cholinergic agonists and vagus nerve stimulation," filed Apr. 24, 2008.
Tracey et al.; U.S. Appl. No. 12/198,808 entitled Devices and methods for inhibiting granulocyte activation by neural stimulation, filed Aug. 26, 2008.
Faltys et al.; U.S. Appl. No. 12/797,452 entitled "Nerve cuff with pocket for leadness stimulator," filed Jun. 9, 2010.
Hatton et al.; Vagal nerve stimulation: overview and implications for anesthesiologists; Int'l Anesthesia Research Society; vol. 103; No. 5; pp. 1241-1249; Nov. 2006.
Hoffer et al.; Implantable electrical and mechanical interfaces with nerve and muscle; Annals of Biomedical Engineering; vol. 8; pp. 351-360; 1980.
Krarup et al.; Conduction studies in peripheral cat nerve using implanted electrodes: I. methods and findings in controls; Muscle & Nerve; vol. 11; pp. 922-932; Sep. 1988.
Loeb et al.; Cuff electrodes for chronic stimulation and recording of peripheral nerve activity; Journal of Neuroscience Methods; vol. 64; pp. 95-103; 1996.
Strojnik et al.; Treatment of drop foot using and implantable peroneal underknee stimulator; Scand. J. Rehab. Med.; vol. 19; p. 37R43; 1987.
Beliavskaia et al.,"On the effects of prolonged stimulation of the peripheral segment of the vagus nerve on blood clotting time under different bodily conditions," Fiziologicheskii Zhurnal SSSR Imeni I.M. Sechenova., vol. 52(11); p. 1315-1321, Nov. 1966.
Kalishevskaya et al.; Neural regulation of the fluid state of the blood; Usp. Fiziol. Nauk;,vol. 13; No. 2; pp. 93-122; 1982.

Kuznik, et al., "Role of the heart and vessels in regulating blood coagulation and fibrinolysis," Kagdiologiia, vol. 13(4): pp. 145-154, 1973.
Kuznik, "Role of the vascular wall in the process of hemostatis," Usp Sovrem Biol.,vol. 75(1): pp. 61-85, 1973.
Pateyuk, et al.,"Treatment of Botkin's disease with heparin," Klin. Med., vol. 51(3): pp. 113-117, 1973.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Zitnik et al.; U.S. Appl. No. 12/874,171 entitled "Prescription pad for treatment of inflammatory disorders," filed Sep. 1, 2010.
Martindale: The extrapharcopoeia; 28th Ed. London; The pharmaceutical press; pp. 446-485; 1982.
Shi et al.; Effects of efferent vagus nerve excitation on inflammatory response in heart tissue in rats with endotoxemia; vol. 15, No. 1; pp. 26-28; 2003 (Eng. Abstract).
Levine, Jacob A.; U.S. Appl. No. 13/338,185 entitled "Modulation of sirtuins by vagus nerve stimulation" filed Dec. 27, 2011.
Nadol et al., "Surgery of the Ear and Temporal Bone," Lippinkott Williams & Wilkins, 2nd Ed., 2005, (Publication date: Sep. 21, 2004), p. 580.
Tracey, K. J. et al., Physiology and immunology of the cholinergic antiinflammatory pathway; J Clin Invest.; vol. 117: No. 2; pp. 289-296; Feb. 2007.
Van Der Horst et al.; Stressing the role of FoxO proteins in lifespan and disease; Nat Rev Mol Cell Biol.; vol. 8; No. 6; pp. 440-450; Jun. 2007.
Levine et al.; U.S. Appl. No. 13/851,013 entitled "Devices and methods for modulation of bone erosion," filed Mar. 26, 2013.
Levine et al.; U.S. Appl. No. 13/467,928 entitled "Single-Pulse Activation of the Cholinergic Anti-Inflammatory Pathway to Treat Chronic Inflammation," filed May 9, 2012.
Robinson et al.; Studies with the Electrocardiograph on the Action of the Vagus Nerve on the Human Heart; J Exp Med; 14(3):217-234; Sep. 1911.
Tracey et al.; U.S. Appl. No. 14/569,504 entitled "Inhibition of inflammatory cytokine production by cholinergic agonists and vagus nerve stimulation," filed Dec. 12, 2014.
Gao et al.; Investigation of specificity of auricular acupuncture points in regulation of autonomic function in anesthetized rats; Autonomic Neurosc.; 138(1-2); pp. 50-56; Feb. 29, 2008.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Peuker; The nerve supply of the human auricle; Clin. Anat.; 15(1); pp. 35-37; Jan. 2002.
Tekdemir et al.; A clinico-anatomic study of the auricular branch of the vagus nerve and arnold's ear-cough reflex; Surg. Radiol. Anat.; 20(4); pp. 253-257; Mar. 1998.
Zamotrinsky et al.; Vagal neurostimulation in patients with coronary artery disease; Auton. Neurosci.; 88(1-2); pp. 109-116; Apr. 2001.
Zitnik et al.; U.S. Appl. No. 14/630,613 entitled "Vagus nerve stimulation screening test," filed Feb. 24, 2015.
Clark et al.; Enhanced recognition memory following vagus nerve stimulation in human subjects; Nat. Neurosci.; 2(1); pp. 94-98; Jan. 1999.
Dorr et al.; Effect of vagus nerve stimulation on serotonergic and noradrenergic transmission; J. Pharmacol. Exp. Ther.; 318(2); pp. 890-898; Aug. 2006.
Groves et al.; Recordings from the rat locus coeruleus during acute vagal nerve stimulation in the anaesthetised rat; Neuroscience Letters; 379(3); pp. 174-179; May 13, 2005.
Neuhaus et al.; P300 is enhanced in responders to vagus nerve stimulation for treatment of major depressive disorder; J. Affect. Disord.; 100(1-3); pp. 123-128; Jun. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Tracey et al.; U.S. Appl. No. 15/716,408 entitled "Treatment of bleeding by non-invasive stimulation," filed Sep. 26, 2017.

(56) References Cited

OTHER PUBLICATIONS

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Pavlov et al.; Controlling inflammation: the cholinergic anti-inflammatory pathway; Biochem. Soc. Trans.; 34(Pt 6); pp. 1037-1040; Dec. 2006.

Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

Stevens et al.; The anti-inflammatory effect of some immunosuppressive agents; J. Path.; 97(2); pp. 367-373; 1969 (year of pub. sufficiently earlier than effective US filing date and any foreign priority date).

Cavaillon et al.; The pro-inflammatory cytokine casade; Immune Response in the Critically Ill; Springer-Verlag Berlin Hiedelberg; pp. 37-66; Jan. 21, 2002.

Pongratz et al.; The sympathetic nervous response in inflammation; Arthritis Research and Therapy; 16(504); 12 pages; retrieved from the internet (http://arthritis-research.eom/content/16/6/504); Jan. 2014.

Faltys et al.; U.S. Appl. No. 16/005,191 entitled "Neural stimulation devices and systems for treatment of chronic inflammation," filed Jun. 11, 2018.

Faltys et al.; U.S. Appl. No. 16/292,144 entitled "Nerve cuff with pocket for leadless stimulator," filed Mar. 4, 2019.

Zitnik et al.; U.S. Appl. No. 16/356,906 entitled "Batteryless Implantable Microstimulators," filed Mar. 18, 2019.

Faltys et al.; U.S. Appl. No. 16/544,882 entitled "Neural stimulation devices and systems for treatment of chronic inflammation," filed Aug. 19, 2019.

Manogue, U.S. Appl. No. 16/582,726 entitled "Methods and apparatuses for reducing bleeding via coordinated trigeminal and vagal nerve stimulation," filed Sep. 25, 2019.

Faltys et al.; U.S. Appl. No. 16/785,400 entitled "Systems and methods for establishing a nerve block," filed Feb. 7, 2020.

Koopman et al., Pilot study of stimulation of the cholinergic anti-inflammatory pathway with an implantable vagus nerve stimulation device in patients with rheumatoid arthritis: 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulaton-device-in-patients-with-rheumatoid-arthritis); (Abstract Only); on Sep. 24, 2020.

Pavlov et al.; The cholinergic anti-inflammatory pathway; Brain, Behavior, and Immunity; 19; p. 493-499; Nov. 2005.

Tracey et al.; U.S. Appl. No. 17/170,772 entitled "Treatment of bleeding by non-invasive stimulation," filed Feb. 8, 2021.

\* cited by examiner

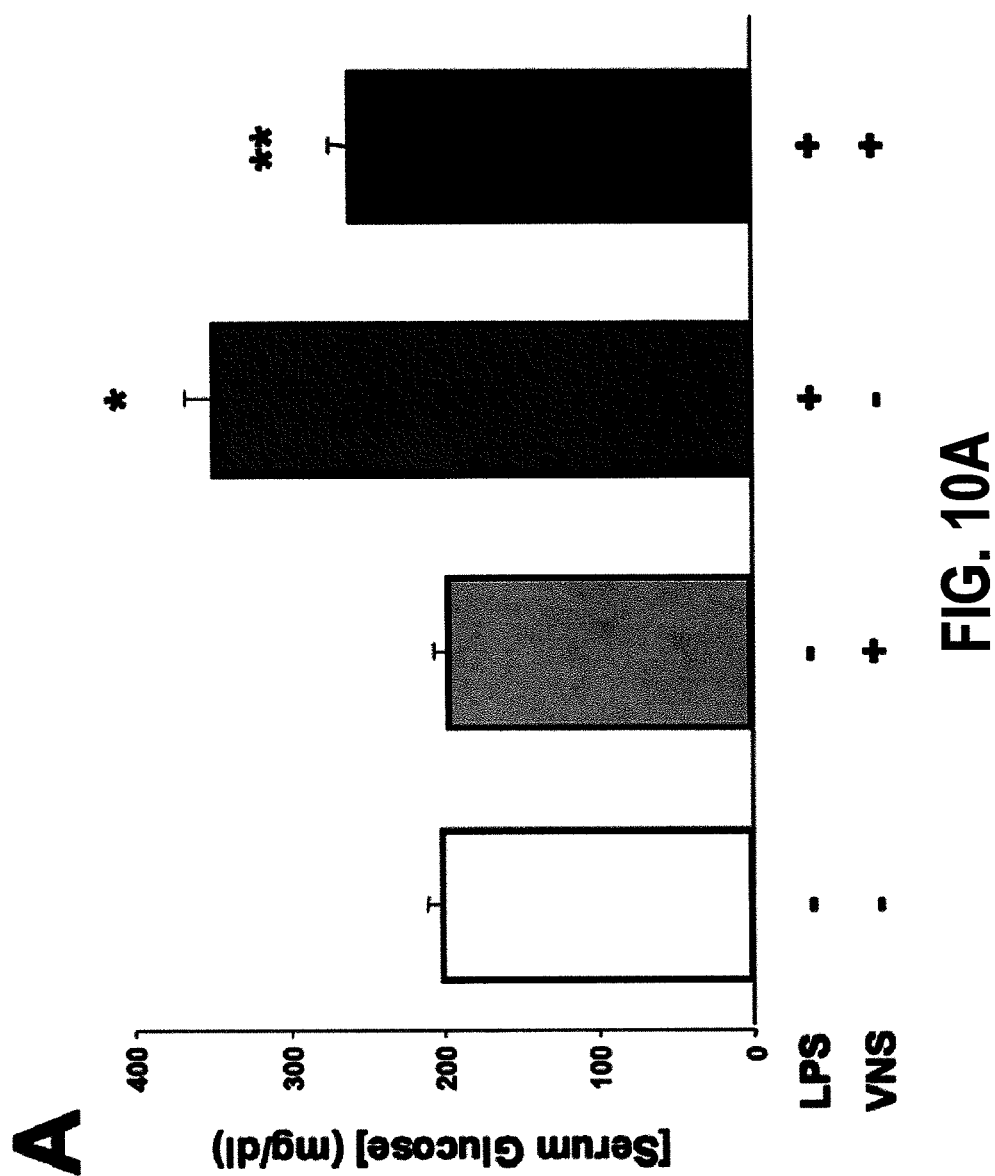

TREATING INFLAMMATORY DISORDERS BY STIMULATION OF THE CHOLINERGIC ANTI-INFLAMMATORY PATHWAY

CROSS REFERENCE TO RELATED APPLICATIONS

This patent application claims priority as a continuation-in-part of U.S. patent application Ser. No. 11/318,075, filed Dec. 22, 2005, which claims priority to provisional patent application 60/639,332, field Dec. 27, 2004. This patent application also claims priority to U.S. Provisional Patent Application Ser. No. 60/982,681, filed Oct. 25, 2007.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The methods, systems and devices described herein are directed to treatment of inflammatory disorders by appropriate and controlled stimulation of all or a portion of the cholinergic anti-inflammatory pathway.

BACKGROUND OF THE INVENTION

Vertebrates achieve internal homeostasis during infection or injury by balancing the activities of pro-inflammatory and anti-inflammatory pathways. In many disease conditions, this internal homeostasis becomes out of balance. For example, endotoxin (lipopolysaccharide, LPS) produced by Gram-negative bacteria activates macrophages to release cytokines that are potentially lethal (Tracey, K. J. et al., Science, 234:470-74 (1986); Dinarello, C. A., FASEB J., 8:1314-25 (1994); Wang, H., et al., Science, 285:248-51 (1999); Nathan, C. F., J. Clin. Invest., 79:319-26 (1987)).

Inflammation and other deleterious conditions (such as septic shock caused by endotoxin exposure) are often induced by pro-inflammatory cytokines, such as tumor necrosis factor (TNF; also known as TNF-α or cachectin), interleukin (IL)-1α, IL-1β, IL-6, IL-8, IL-18, interferon-γ, platelet-activating factor (PAF), macrophage migration inhibitory factor (MIF), and other compounds. Certain other compounds, for example high mobility group protein 1 (HMG-1), are induced during various conditions such as sepsis and can also serve as pro-inflammatory cytokines. Pro-inflammatory cytokines contribute to various disorders, notably sepsis, through their release during an inflammatory cytokine cascade. Inflammatory cytokine cascades contribute to deleterious characteristics, including inflammation and apoptosis, of numerous disorders.

Although the pro-inflammatory cytokines typically aid in protecting against invasive pathogens, failure to resolve the initial infection can result in overproduction and spillage of cytokines into the systemic circulation, causing shock and lethal tissue injury. Counter-regulatory mediators, including glucocorticoids and interleukin-10, function to limit excessive pro-inflammatory responses. However, these humoral "anti-inflammatory" mechanisms can also predispose the host to secondary infections and increase overall morbidity and mortality.

It has recently been shown that the nervous system regulates systemic inflammation through an α7 nicotinic acetylcholine receptor (α7nAChR)-dependent vagus nerve pathway to the spleen, termed the cholinergic anti-inflammatory pathway (Huston J M, Ochani M, Rosas-Ballina M, et al., J Exp Med 2006; 203:1623-1628 (2006)). This anti-inflammatory pathway may form an inflammatory reflex, including the vagus nerve, the splenic nerve, the hepatic nerve, the facial nerve, and the trigeminal nerve.

Electrical stimulation of the anti-inflammatory pathway (e.g., the vagus nerve or other portions of the anti-inflammatory reflex such as the splenic nerve, the hepatic nerve, etc.) inhibits pro-inflammatory cytokine production and prevents tissue injury in experimental models of systemic inflammation. Such stimulation fails to regulate pro-inflammatory responses in α7nAChR-deficient or splenectomized animals, or following interruption of the common celiac vagus branches, indicating that the cholinergic anti-inflammatory pathway requires specific molecular, organ, and neural components.

Pharmacologic α7nAChR agonists may mimic the effects of stimulation, and administration of these agents to mice with polymicrobial sepsis improves survival and attenuates production of high mobility group box 1 (HMGB1), a critical mediator of lethal sepsis. It is unclear, however, whether chronic vagus nerve stimulation can also improve survival during lethal sepsis.

Furthermore, the components of the cholinergic anti-inflammatory pathway, such as the vagus nerve, also subsume a number of other physiological roles and functions. In particular, the vagus nerve activation and/or inhibition is involved in regulating cardiac function (e.g., heart rate), larynx function, diaphragm activity (respiration), stomach (digestion) and includes both motor and sensory functions, as well as being implicated in brain activity including consciousness. Thus, the stimulation of any portion of the cholinergic anti-inflammatory pathway, and particularly the vagus nerve, must be performed specifically and precisely, in order to avoid disrupting or undesirably modifying any of these other functions.

Described herein are methods, systems and devices for specifically regulating the cholinergic anti-inflammatory pathway by precisely regulated and applied stimulation. In particular, described herein are methods, systems and devices for treating inflammation by electrical stimulation that are sufficient to inhibit inflammation without substantially affecting heart rate or other cardiac parameters, digestion, respiration, or other biological systems regulated by components of the inflammatory reflex such as the vagus nerve.

For example, the methods described herein provide methods for inhibition of pro-inflammatory cytokine production and protection against the long and short-term effects of the pro-inflammatory cytokines.

SUMMARY OF THE INVENTION

In general, described herein are methods, systems and devices for treating cytokine-mediated inflammatory conditions. These methods, systems and devices typically stimulate all or a portion of a patient's inflammatory reflex (e.g., the vagus nerve), to inhibit inflammation, pro-inflammatory cytokine production or release, or the pro-inflammatory cytokine cascade. For example, the inhibitory stimulation described herein includes extremely low duty-cycle stimulation, such as stimulation of the vagus nerve at levels that do not provoke other non-immune, biological effects mediated by the vagus nerve (e.g., blood pressure, heart rate, etc.). Also described is effective repeated and/or chronic stimulation of the vagus nerve. For example, the effective extremely low-intensity vagus stimulation, and particularly chronic (or repeated) stimulation of the cholinergic anti-inflammatory pathway, may include low or extremely low duty-cycle (e.g., less than 1%, less than 0.01%, less than 0.001%, less than 0.0001%) stimulation of the vagus nerve to effectively inhibit or beneficially modulate inflammation or cytokine-mediated inflammatory conditions.

Using the methods and devices described herein, inflammatory disorders can be treated in a subject by electrically stimulating the cholinergic anti-inflammatory pathway, including, without limitation, the vagus nerve. Surprisingly, it has also been discovered that the parameters of an electrical signal sufficient to treat inflammatory disorders are significantly milder than the parameters previously shown to inhibit the inflammatory cytokine cascade. Thus, it has been discovered that inflammatory disorders can be treated by an electrical signal having its current or voltage significantly smaller than electrical signals previously shown to inhibit inflammation.

Described herein are methods of treating an inflammation in a patient. For example, the method may include the steps of: stimulating the patient's vagus nerve with an electrical signal, wherein the signal voltage is between about 0.01 Volt to 1 Volt, the pulse width is from 0.1 ms to 5 ms; the signal frequency is from 0.1 Hz to 30 Hz; signal on-time is from 1 second to 120 seconds; and waiting for an off-time of at least 2 hours before re-stimulating the patient's vagus nerve. In some variations, the method may also include the step of monitoring one or more non-inflammatory vagal efferent effects (e.g., heart rate, blood pressure, heart rate variability, digestive processes) and modifying the stimulation so that it does not affect such parameters.

In some variations, the stimulation is transcutaneous stimulation of the vagus nerve. For example, the stimulation may be transdermal. In some variations, the intensity of the stimulation (e.g., the voltage between 0.01 and 1 V) is determined at the nerve. Thus the voltage applied to the electrode(s) may be adjusted based on the attenuation through the tissue.

The off-time before the vagus nerve is re-stimulated may be from about 2 hours to about 48 hours. In general "off-time" is the time between "stimulation-on" periods or burst of pulses. For example, a burst of signals at 30 Hz for 120 seconds may be followed by an off-time of 2 or more hours. During the off-time, a controller for the system may be locked so that additional stimulation cannot be applied. In some variations, the off-time before the vagus nerve is re-stimulated is between about 16 and about 30 hours.

The method may also include the step of monitoring the effect of the stimulation on inflammation in the patient. For example, the level of a pro-inflammatory cytokine prior to stimulation may be determined, as well as the level of a pro-inflammatory cytokine during/after stimulation, and the levels may be compared. The intensity and/of frequency of stimulation may be adjusted based on the monitoring.

Also described herein are methods of treating inflammation in a patient, including the steps of: applying an electrode to a patient suffering from or at risk for a chronic inflammatory disorder; stimulating the patient's vagus nerve with an electrical signal from the electrode, wherein the signal voltage is from 0.01 Volt to 1 Volt, pulse width is from 0.1 ms to 5 ms; signal frequency is from 0.1 Hz to 30 Hz; signal on-time is from 1 second to 120 seconds; and waiting for an off-time of at least 2 hours before re-stimulating the patient's vagus nerve.

As mentioned above, in some variations, the method may be transcutaneous stimulation.

The chronic inflammatory disorder treated may be selected from the group consisting of: appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease.

The off-time before the vagus nerve is re-stimulated may be from between about 2 hours to about 48 hours. For example, the off-time before the vagus nerve is re-stimulated may be between about 16 and about 30 hours.

Also described herein are methods of treating inflammation in a patient including the steps of: implanting an electrode into a patient suffering from a chronic inflammatory disorder; stimulating the patient's vagus nerve with an electrical signal from the implanted electrode, wherein the signal voltage is from 0.01 Volt to 1 Volt, pulse width is from 0.1 ms to 5 ms; signal frequency is from 0.1 Hz to 30 Hz; signal on-time is from 1 second to 120 seconds; and waiting for an off-time of at least 2 hours before re-stimulating the patient's vagus nerve.

The chronic inflammatory disorder treated may be selected from the group consisting of: appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease.

BRIEF DESCRIPTION OF THE DRAWINGS

FIG. 10A illustrates the beneficial effect of vagus nerve stimulation (VNS) on serum glucose concentrations in lethal endotoxemia. BALB/c mice were subjected to electrical vagus nerve stimulation (30 seconds, 1 V, 5 Hz, 2 milliseconds) following lipopolysaccharide (LPS) administration (7.5 mg/kg, intraperitoneally). Animals were euthanized after 2 hrs. Data are presented as mean±SEM (n=5-8 per group; *p<0.05 vs. control; **p<0.05 vs. LPS).

DETAILED DESCRIPTION OF THE INVENTION

Figure 1:
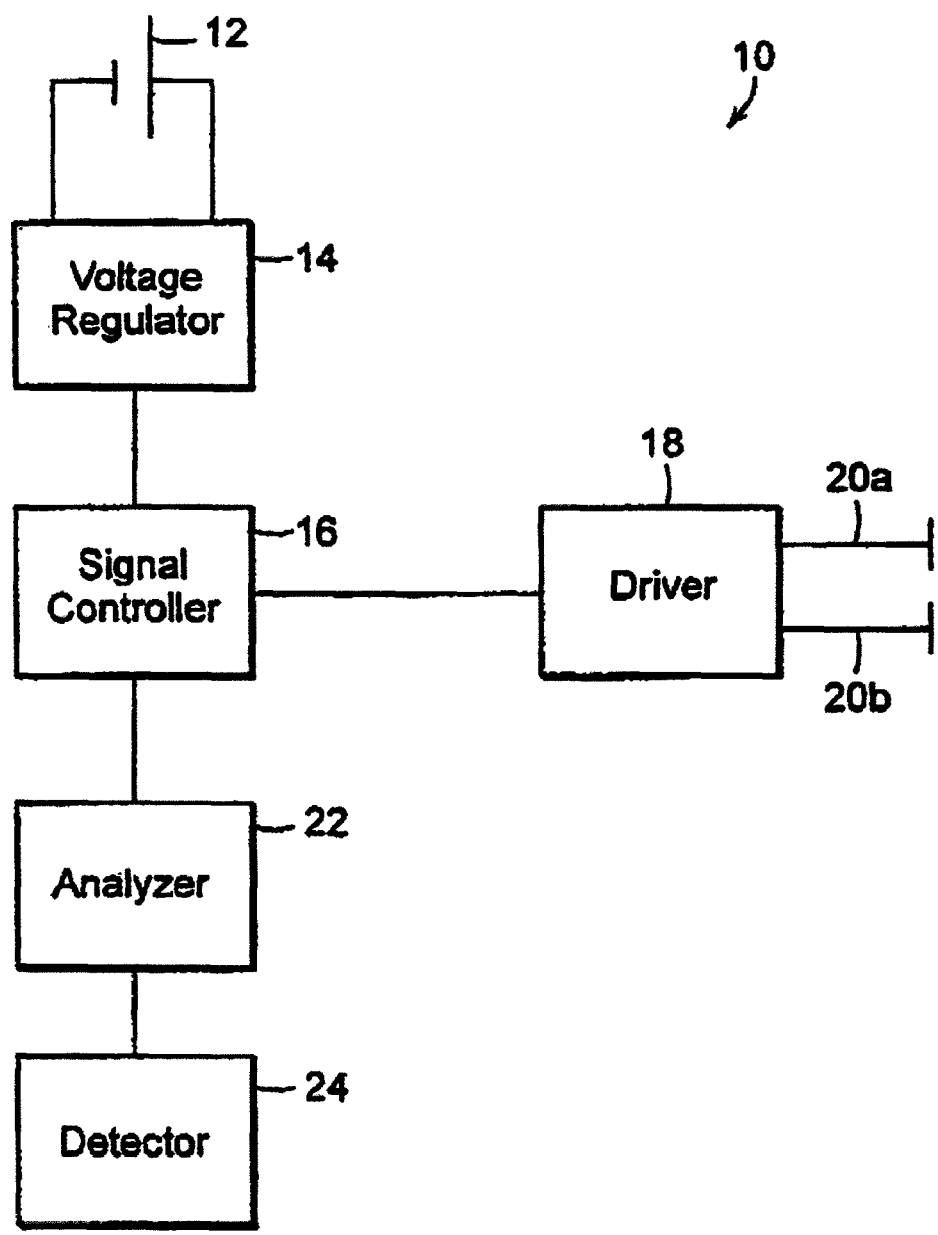
FIG. 1 is a simplified block diagram of one variation of a stimulator (e.g., an electrical stimulus generator) suitable for applying electrical stimulation.

Described herein are devices, systems, and method for decreasing inflammation by appropriate stimulation of one or more components of the cholinergic anti-inflammatory pathway, such as the vagus nerve. In particular, methods of stimulating the vagus nerve to decrease or suppress the release of pro-inflammatory cytokines are described.

Direct (e.g. electrical or mechanical) stimulation of vagus nerve of a subject alleviates the symptoms of inflammatory disorders. As used herein, a "subject" is preferably a mammal, more preferably a human patient but can also be a companion animal (e.g., dog or cat), a farm animal (e.g., horse, cow, or sheep) or a laboratory animal (e.g., rat, mouse, or guinea pig). Preferable, the subject is human. As used herein, the term "vagus nerve" is used in its broadest sense, and may include any nerves that branch off from the main vagus nerve, as well as ganglions or postganglionic neurons that are connected to the vagus nerve. The vagus nerve is also known in the art as the parasympathetic nervous system and its branches, and the cholinergic nerve. The vagus nerve innervates principal organs including, the pharynx, the larynx, the esophagus, the heart, the lungs, the stomach, the pancreas, the spleen, the kidneys, the adrenal glands, the small and large intestine, the colon, and the liver. Stimulation can be accomplished by direct or indirect stimulation of the vagus nerve or an organ served by the vagus nerve.

In some variations, the stimulation is calibrated or controlled so that it does not substantially affect any target or efferent except those related to inflammation. For example, the stimulation provided to the vagus nerve may be below the threshold or frequency for affecting other vagus nerve-mediated effects, such as changes in heart rate, blood pressure, etc.

As used herein, "direct stimulation" of the vagus nerve may mean activating or stimulating the vagus nerve by non-pharmacological means such as electrical, mechanical (e.g., massage or vibration), heat or UV irradiation. Activation can be accomplished by direct or indirect stimulation of the vagus nerve or an organ served by the vagus nerve. The vagus nerve innervates principal organs including, the pharynx, the larynx, the esophagus, the heart, the lungs, the stomach, the pancreas, the spleen, the kidneys, the adrenal glands, the small and large intestine, the colon, and the liver.

The disclosed methods include stimulating the any portion of the cholinergic anti-inflammatory pathway, including the vagus. For example, the entire vagus nerve (i.e., both the afferent and efferent nerves) may be stimulated, or efferent nerve bundles may be isolated and then stimulated directly. The latter method can be accomplished by separating the afferent from the efferent fibers in an area of the nerve where both types of fibers are present. Alternatively, the efferent fibers are stimulated where no afferent fibers are present, for example close to the target organ served by the efferent fibers. The efferent fibers can also be activated by stimulating the target organ directly, e.g., electrically, thus stimulating the efferent fibers that serve that organ. In other embodiments, the ganglion or postganglionic neurons of the vagus nerve can be stimulated. The vagus nerve can also be cut and the distal end can be stimulated, thus only stimulating efferent vagus nerve fibers.

The cholinergic anti-inflammatory pathway (e.g., vagus nerve) can be stimulated by numerous methods including manually, mechanically, electrically or by electromagnetic radiation. Mechanical means of nerve stimulation include, without limitation, stimulation by needle (e.g., acupuncture). There is evidence that response to acupuncture may be at least partially mediated by the vagus nerve. For example, it has been shown that the response to electroacupuncture is attenuated after vagotomy (Noguchi et al, Jpn. J. Physiol. 46(1): 53-58 (1996)). Mechanical stimulation may also include nerve stimulation using ultrasound as described, for example in Norton, BioMedical Engineering 2(1): 6 (2003). Stimulation of the vagus nerve using heat or electromagnetic radiation includes, without limitation, applying heat or infrared, visible, ultraviolet, or other electromagnetic frequencies from an energy source. The vagus nerve may also be stimulated by magnetic stimulation; a description of magnetic nerve stimulation is provided in Hsu et al, IEEE Trans Biomed Eng 50(11): 1276-85 (2003). The entire teachings of these publications are incorporated herein by reference.

The site of stimulation of the cholinergic anti-inflammatory pathway (e.g., of the vagus nerve) may be in the cervical region (in the neck) and a region peripheral and distal of the cervical region including, supra-diaphragmatical or sub-diaphragmatical regions. Peripheral, distal locations include branches of the vagus nerve that innervate organs, including but not limited to, the spleen, the small intestine and the large intestine. The vagus nerve may also be stimulated endotracheally or transesophageally. Endotracheal or transesophageal vagal nerve stimulation may be accomplished using an endotracheal/esophageal nerve stimulator (described, for example, in U.S. Pat. No. 6,735,471, incorporated herein by reference in its entirety). The vagus nerve can be stimulated transesophageally using one or more esophageal electrodes (described, for example, in U.S. Pat. No. 5,571,150). The vagus nerve can also be stimulated using a transcutaneous nerve stimulator (as described for example in U.S. Pat. No. 6,721,603, incorporated herein by reference in its entirety) or a percutaneous nerve stimulator. In one embodiment, the vagus nerve is stimulated in the cervical region. In another embodiment, the vagus nerve is stimulated at a peripheral, distal location. In another embodiment, the vagus nerve is stimulated in the brain by the device.

According to one embodiment, the vagus nerve is stimulated by delivering an electrical signal generated by any suitable vagus nerve stimulators. For example, a commercial vagus nerve stimulator such as the Cyberonics NCP, or an electric probe can be used.

Examples of suitable vagus nerve stimulators are described, for example, in U.S. Pat. Nos. 4,702,254; 5,154,172; 5,231,988; 5,330,507; 6,473,644; 6,721,603; 6,735,471; and U.S. Pat. App. Pub. 2004/0193231. The teachings of all of these publications are incorporated herein by reference in their entirety.

The vagus nerve can be stimulated by means of either an implanted device or a device worn external to the patient's body, such as Cyberonics NCP device described in U.S. Pat. No. 5,231,988 or a Medtronic device described in U.S. Pat. No. 5,330,507. Both patents describe apparati for stimulating the right or left vagus nerve with continuous and/or phasic electrical signal.

A schematic diagram of one variation of an electrical signal generator device suitable for practicing the methods described herein is shown in FIG. 1. Referring to FIG. 1, a typical signal generator 10 includes a battery (or set of batteries) 12, which may be of any type conventionally employed for powering medical electronic devices. Battery 12 is connected to a voltage regulator 14. Regulator 14 smoothes the battery output to produce steady output voltage as well as provides voltage multiplication or division if necessary.

Regulator 13 supplies power to signal controller 16. Signal controller 16 can includes a microprocessor. Signal controller 16 controls functions of the device such as output signal current or voltage, output signal frequency, output signal pulse width, output signal on-time, output signal off-time. Controller 16 can be programmed to control daily times for continuous or periodic modulation of vagal activity as well as output signal start delay time. Such programmability allows the output signal to be adjusted for the treatment regimen. The controller 16 may also limit the stimulation, so that it does not exceed a maximum level for intensity (e.g., voltage) or frequency (including on and/or off time, etc.). In some variations, the controller controls the stimulation by regulating the output to the electrodes (via Driver 18) so that the signal delivered to the tissue (e.g., vagus nerve) is within a predetermined range.

When device 10 is implanted, a built-in antenna (not shown) can be used to enable communication between device 10 and external programming or monitoring devices (not shown).

Signal controller 16 controls driver 18 which generates the desired electrical signal. The output signal is applied to the patient's body via electrodes 20a and 20b.

Analyzer 22 can be provided to process any relevant physiological parameters of a patient such as heart rate or blood pressure detected by detector 24.

Figure 2:
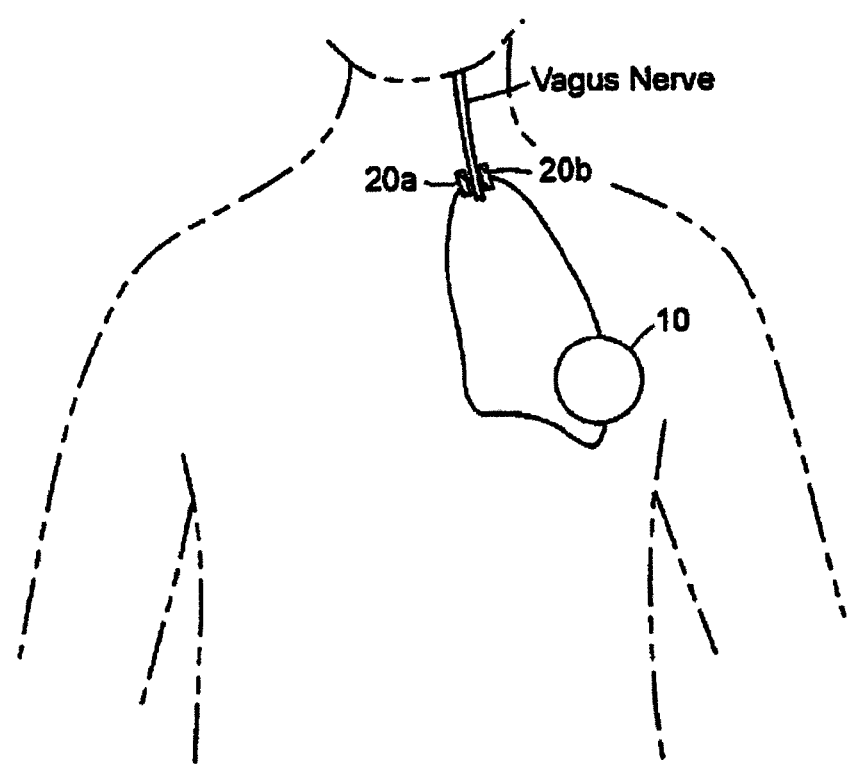
FIG. 2 shows one suitable location for vagus nerve stimulation (VNS) using an electric signal generator and electrodes implanted in the patient's body.

As mentioned above, device 10 can be worn external to the patient's body or can be implanted. FIG. 2 illustrates one embodiment of an implantable device for practicing the methods described herein, where signal generator 10 is implanted in the patient's chest in a pocket formed by the surgeon just below the skin. One suitable location for the generator is in the patient's chest, as a pacemaker pulse generator would be implanted, with the electrodes 20a and 20b implanted in the patient's neck.

Electrodes 20a and 20b can be bipolar stimulating electrodes of the type described in U.S. Pat. No. 4,573,481, incorporated herein by reference in its entirety. In this embodiment, electrodes form an assembly which is surgically implanted on the vagus nerve in the patient's neck. The two electrodes are wrapped around the vagus nerve, and the assembly is secured to the nerve by a spiral anchoring tether as disclosed in U.S. Pat. No. 4,979,511, incorporated herein by reference in its entirety.

Structurally, the electrode assembly can comprise two ribbons of platinum which are individually bonded to each of the two spiral loops wrapped around the vagus nerve. Each loop further includes silicone rubber. An additional helical loop that includes silicon rubber is provided to tether the electrode assembly to the vagus nerve. The inner diameter of the helical bipolar electrodes may typically be about two millimeters (mm), and an individual spiral is about seven mm long (measured along the axis of the nerve).

Instead of implanting the electrode assembly in the patient's neck, the assembly may be implanted on the vagus nerve as it innervates any of the organs listed above. The implantation of electrodes 20a and 20b is accomplished in substantially the same manner as was described for the neck location.

Figure 3:
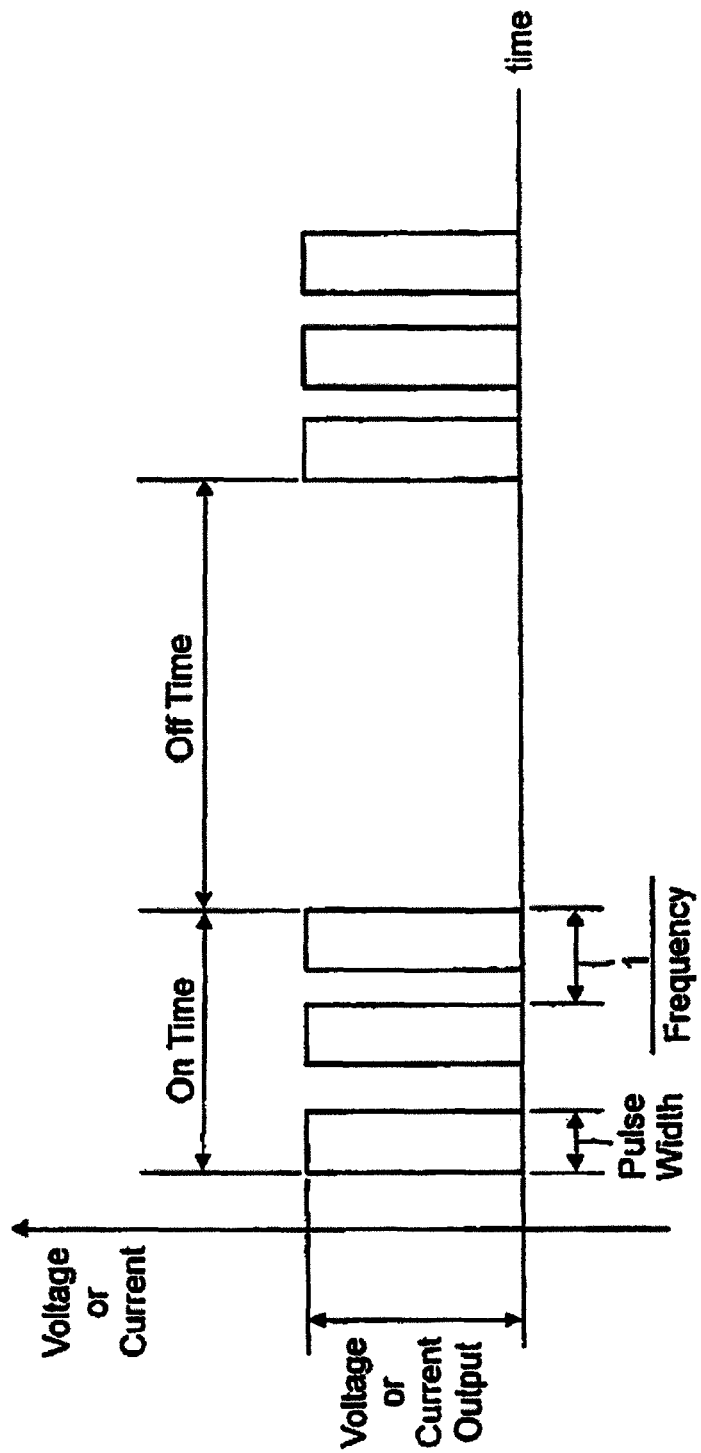
FIG. 3 is an illustrative idealized electrical output signal waveform that may be useful for clarifying relevant parameters of the stimulation signal.
Figure 4:
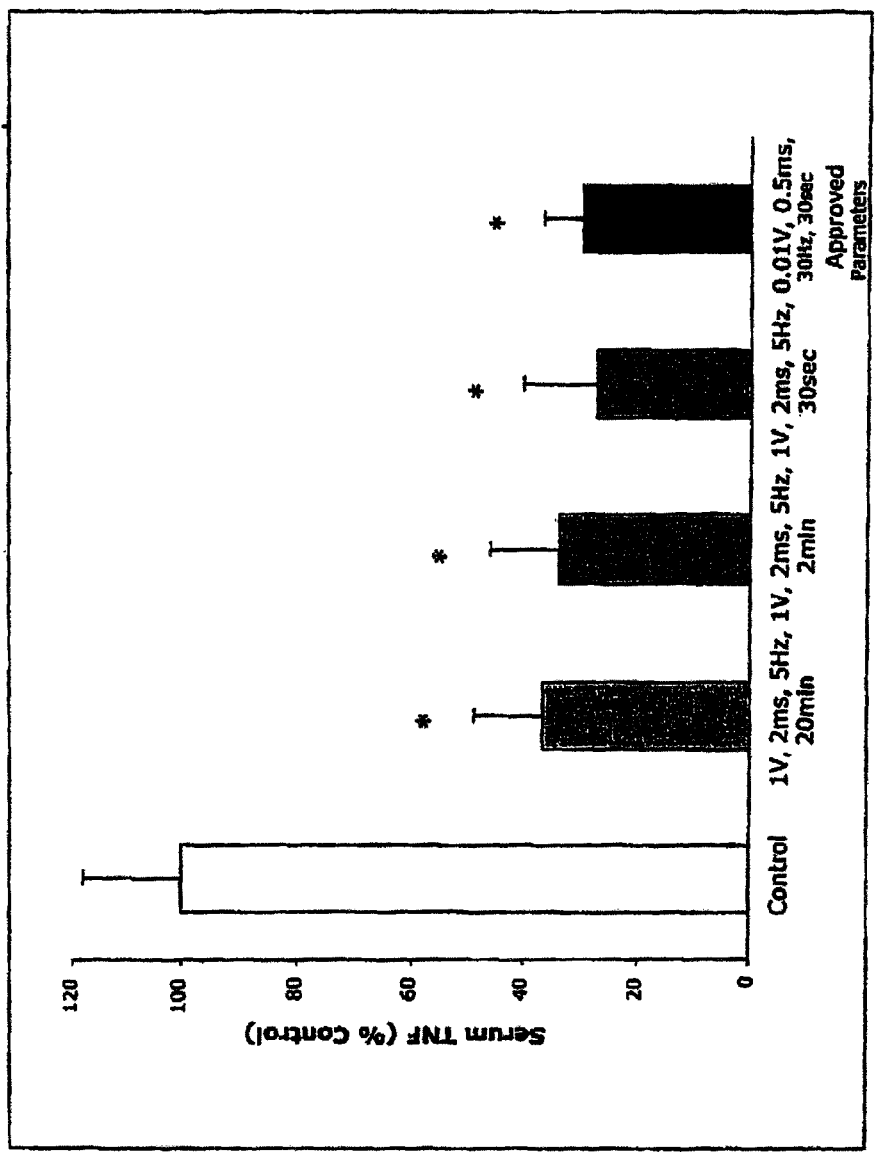
FIG. 4 is a bar plot illustrating the effect of the vagal electrical stimulation on endotoxemia as measured by a reduced percentage of serum TNF level.

The operation of signal generator 10 to control and treat inflammatory disorders will be described by reference to the signal waveform and parameters shown in FIG. 3. The latter is an idealized representation of the output signal delivered by driver 18. FIG. 3 serves to clarify terminology used to refer to the parameters of an electrical signal. Such parameters include signal on-time, signal off-time, signal frequency, signal pulse width, signal current, and signal voltage. Treatment of inflammatory disorders can be accomplished by applying voltage to electrodes 20a and 20b as well as by driving a current between electrodes 20a and 20b. While the pulses shown in FIG. 3 have positive voltage or current output, electrical signals having negative outputs can also be used.

Signal controller 16 controls the output signal by limiting the output to a suitable range of parameters specified above with reference to FIG. 3. A range of each parameter can be chosen independently from any other parameter. Alternatively, a combination of ranges for any number of parameters can be chosen. Preferred examples of specific values for the parameters and combinations of parameters as provided below with respect to the controller are also applicable to the disclosed methods of treatment.

Signal controller can limit signal voltage to a range from about 0.01 Volt to about 1 Volt, preferably to a range from about 0.01 Volt to about 0.1 Volt, more preferably, to a range from about 0.01 Volt to about 0.05 Volt.

Signal controller can limit signal current to a range from about 1 mA to about 100 mA, preferably to a range from about 1 mA to about 10 mA, more preferably to a range from about 1 mA to about 5 mA.

In some embodiments, both signal voltage and signal current are controlled.

In other embodiments, either in addition to or independently from controlling signal voltage, signal current or both, signal controller can further control one or more parameters selected from pulse width, on-time and frequency. Signal controller can limit the pulse width to a range from about 0.1 ms to about 5 ms, preferably to a range from about 0.1 ms to about 1 ms, more preferably to a range from about 0.1 ms to about 0.5 ms. Signal controller can limit signal on-time from about 1 second to about 120 seconds, preferably, to a range of from about 10-seconds to about 60 seconds, more preferably, to a range from about 20 seconds to about 40 seconds. Signal controller can limit signal frequency to a range from about 0.1 Hz to about 30 Hz, preferably, to a range from about 1 Hz to about 30 Hz, more preferably, to a range from about 10 Hz to about 30 Hz.

In other embodiments, either in addition to or independently from controlling signal voltage and/or signal current, as well as signal width, signal frequency and/or signal on-time, signal controller can further control signal off-time. In one embodiment, a subject can be treated with one pulse. In another embodiment, signal controller can limit signal off-time to a range of over 5 minutes, preferably, over 2 hours, more preferably, over 4 hours, even more preferably, over 8 hours, still more preferably, over 12 hours. In another embodiment, signal controller can limit signal off-time to a range of from about 2 hours to about 48 hours, preferably to a range from about 4 hours to about 36 hours, more preferably, to a range from about 6 hours to about 36 hours. In other preferred embodiments, signal controller can limit signal off-time to a range selected from: from about 6 to about 36 hours, from about 12 to about 36 hours, from about 16 to about 30 hours and from about 20 to about 28 hours. Alternatively, signal off-time can be undefined as one skilled in the art will readily determine the desired time interval between two consecutive signals.

As mentioned above, various parameters can be limited to the specified ranges alone or in combination. In one example, signal controller can limit a combination of parameters as follows: signal voltage to a range from about 0.01 Volt to about 1 Volt; pulse width to a range from about 0.1 ms to about 5 ms; signal frequency to a range from about 0.1 Hz to about 30 Hz; signal on-time from about 1 second to about 120 seconds. Signal off-time can be undefined. Alternatively, signal off-time can be limited to a range over about 5 minutes. In other preferred embodiments, signal controller can limit signal off-time to a range selected from: from about 6 to about 36 hours, from about 12 to about 36 hours, from about 16 to about 30 hours and from about 20 to about 28 hours.

In another example, signal controller can limit a combination of parameters as follows: signal current to a range from about 1 mA to about 100 mA; pulse width to a range from about 0.1 ms to about 5 ms; signal frequency to a range from about 0.1 Hz to about 30 Hz; signal on-time from about 1 second to about 120 seconds. Signal off-time can be undefined. Alternatively, signal off-time can be limited to a range over about 5 minutes. In other preferred embodiments, signal controller can limit signal off-time to a range selected from: from about 6 to about 36 hours, from about 12 to about 36 hours, from about 16 to about 30 hours and from about 20 to about 28 hours.

In a preferred embodiment, signal controller can limit a combination of parameters as follows: signal voltage to a range from about 0.01 Volt to about 0.1 Volt; pulse width to a range from about 0.1 ms to about 1 ms; signal frequency to a range from about 1 Hz to about 30 Hz; signal on-time to a range of from about 10 seconds to about 60 seconds; signal off-time to a range of over 2 hours. Alternatively, signal off-time can be undefined. In other preferred embodiments, signal controller can limit signal off-time to a range selected from: from about 6 to about 36 hours, from about 12 to about 36 hours, from about 16 to about 30 hours and from about 20 to about 28 hours.

Alternatively, signal controller can limit a combination of parameters as follows: signal current to a range from about 1 mA to about 10 mA; pulse width to a range from about 0.1 ms to about 1 ms; signal frequency to a range from about 1 Hz to about 30 Hz; signal on-time to a range of from about 10 seconds to about 60 seconds; signal off-time to a range of over 2 hours. Alternatively, signal off-time can be undefined. In other preferred embodiments, signal controller can limit signal off-time to a range selected from: from about 6 to about 36 hours, from about 12 to about 36 hours, from about 16 to about 30 hours and from about 20 to about 28 hours.

More preferably, signal controller can limit a combination of parameters as follows: signal voltage to a range from about 0.01 Volt to about 0.05 Volt; pulse width to a range from about 0.1 ms to about 0.5 ms; signal to a range from about 10 Hz to about 30 Hz; signal on-time to a range from about 20 seconds to about 40 seconds; signal off-time to a range of from about 2 hours to about 24 hours. Alternatively, signal off-time can be undefined. In other preferred embodiments, signal controller can limit signal off-time to a range selected from: from about 6 to about 36 hours, from about 12 to about 36 hours, from about 16 to about 30 hours and from about 20 to about 28 hours. In other preferred embodiments, signal controller can limit signal off-time to a range selected from: from about 6 to about 36 hours, from about 12 to about 36 hours, from about 16 to about 30 hours and from about 20 to about 28 hours.

Alternatively, signal controller can limit a combination of parameters as follows: signal current to a range from about 1 mA to about 5 mA; pulse width to a range from about 0.1 ms to about 0.5 ms; signal to a range from about 10 Hz to about 30 Hz; signal on-time to a range from about 20 seconds to about 40 seconds; signal off-time to a range of from about 2 hours to about 24 hours. Alternatively, signal off-time can be undefined. In other preferred embodiments, signal controller can limit signal off-time to a range selected from: from about 6 to about 36 hours, from about 12 to about 36 hours, from about 16 to about 30 hours and from about 20 to about 28 hours.

As used herein, "treatment" may include prophylactic and therapeutic treatment. "Prophylactic treatment" refers to treatment before onset of an inflammatory condition to prevent, inhibit or reduce its occurrence. Therapeutic treatment is treatment of a subject who is already experiencing an inflammatory disorder.

"Inflammatory disorders" are usually mediated by an inflammatory cytokine cascade, defined herein as an in vivo release from cells of at least one pro-inflammatory cytokine in a subject, wherein the cytokine release affects a physiological condition of the subject. Non-limiting examples of cells that produce pro-inflammatory cytokines are monocytes, macrophages, neutrophils, epithelial cells, osteoblasts, fibroblasts, smooth muscle cells, and neurons.

As used herein, a "cytokine" is a soluble protein or peptide which is naturally produced by mammalian cells and which act in vivo as humoral regulators at micro- to pico-molar concentrations. Cytokines can, either under normal or pathological conditions, modulate the functional activities of individual cells and tissues. A pro-inflammatory cytokine is a cytokine that is capable of causing any of the physiological reactions associated with inflammation, such as: vasodialation, hyperemia, increased permeability of vessels with associated edema, accumulation of granulocytes and mononuclear phagocytes, or deposition of fibrin. In some cases, the pro-inflammatory cytokine can also cause apoptosis, such as in chronic heart failure, where TNF has been shown to stimulate cardiomyocyte apoptosis. Non-limiting examples of pro-inflammatory cytokines are tumor necrosis factor (TNF), interleukin (IL)-1.alpha., IL-1.beta., IL-6, IL-8, IL-18, interferon-γ, HMG-1, platelet-activating factor (PAF), and macrophage migration inhibitory factor (MIF). In one embodiments, the pro-inflammatory cytokine that is inhibited by cholinergic agonist treatment is TNF, an IL-1, IL-6 or IL-18, because these cytokines are produced by macrophages and mediate deleterious conditions for many important disorders, for example endotoxic shock, asthma, rheumatoid arthritis, inflammatory bile disease, heart failure, and allograft rejection. In most preferred embodiments, the pro-inflammatory cytokine is TNF.

Pro-inflammatory cytokines are to be distinguished from anti-inflammatory cytokines, such as IL-4, IL-10, and IL-13. In preferred embodiments, release of anti-inflammatory cytokines is not inhibited by cholinergic agonists.

When referring to the effect of the vagus nerve stimulation on an inflammatory disorder, the use of the terms "treatment", "inhibition", "decrease" or "attenuation" encompasses at least a small but measurable reduction in the symptoms associated with the disorder being treated.

"Treatment" includes both therapeutic and prophylactic treatments.

Described herein are methods of treatment of inflammatory disorders or conditions mediated by an inflammatory cytokine cascade. In one aspect, the disorder is not ileus, asthma or cystic fibrosis.

In another embodiment, the methods described herein may be methods of treating ileus. As used herein, "ileus" means a short term cessation (less than one month, typically, less than 2 weeks, often less than 1 week) of function of bowels not caused by chronic condition such as gastric ulcer, gastroesophageal reflux, diabetic gastroparesis, postvagotomy, and postgastrectomy. In one embodiment ileus is characterized by inflammation of intestinal smooth muscles.

The methods describe herein can be used to treat ileus caused by manipulation of the bowels during abdominal surgery ("post-operative ileus"), or administration of narcotics or chemotherapeutic agents such as during cancer chemotherapy. Successful treatment of ileus includes reduction and alleviation of symptoms of ileus. The terms "reduction" or "alleviation", when referring to symptoms of ileus in a subject, encompass reduction in measurable indicia over non-treated controls. Such measurable indicia include, but are not limited to retention time of gastric content after gavage and myeloperoxidase activity (units per gram) in the gastrointestinal musculature. In preferred embodiments, the measurable indicia are reduced by at least 20% over non-treated controls; in more preferred embodiments, the reduction is at least 70%; and in still more preferred embodiments, the reduction is at least 80%. In a most preferred embodiment, the symptoms of ileus are substantially eliminated.

In one embodiment, the ileus to be treated is a post-operative ileus, i.e. ileus that occurs after abdominal surgery.

With respect to ileus, "treatment" includes pre-operative, peri-operative and post-operative treatment of ileus. Thus, "treatment" means prophylactic treatment of subjects at risk for ileus, for example, a subject undergoing abdominal surgery, experiencing abdominal surgery, or being administered narcotics or chemotherapeutic agents. With respect to ileus, "prophylactic treatment" refers to treatment before onset of ileus to prevent, inhibit or reduce the occurrence of ileus. For example, a subject at risk for ileus, such as a subject undergoing abdominal surgery, or about to undergo abdominal surgery, or being (or about to be) administered narcotics or chemotherapeutic agents can be prophylactically treated according to the method described herein prior to the anticipated onset of ileus. For example, a subject about to undergo surgery can be treated up to eight days before surgery, up to seven days before surgery, up to six days before surgery, up to five days before surgery, up to four days before surgery, up to three days before surgery, 48 hours prior to surgery, up to 36 hours prior to surgery, up to 24 hours prior to surgery, up to 12 hours prior to surgery, up to 6 hours before surgery, up to 3 hours before surgery, up to 2 hours before surgery, up to one hour before surgery and up to the onset of surgery. In another example, a subject can be treated during the surgery or administration of narcotics or chemotherapeutic agents. In another embodiment, the subject can be treated after the completion of surgery of administration of narcotics or chemotherapeutic agents. For example, a subject can be treated immediately after surgery, up to one hour after surgery, up to 2 hours after surgery, up to 3 hours after surgery, up to 6 hours after surgery, up to 12 hours after, up to 24 hours after, up to 36 hours after, up to 48 hours after surgery, up to three days after surgery, up to four days after surgery, up to five days after surgery, up to six days after surgery, up to seven days after surgery or up to eight days after surgery. "Treatment" of ileus also includes therapeutic treatment, where the subject is already experiencing ileus.

In one example, the subject can be treated pre-operatively, post-operatively, or peri-operatively once, twice, three times, four times or more than four times during the intervals described above. Alternatively, the subject can be treated by any combination of pre-operative, post-operative or peri-operative regimens during the intervals described above.

Preferably, ileus is treated by stimulating the vagus nerve endotracheally or transesophageally. Any device capable of performing this function can be employed. An example of an endotracheal/esophageal nerve stimulator is described in U.S. Pat. No. 6,735,471, incorporated herein by reference in its entirety.

Also described herein is the use of any of the devices described above in the manufacture of a therapeutic article for treating inflammatory disorders in a subject, wherein the device, in operation, directly or indirectly stimulates the vagus nerve to treat inflammatory disorders. The term "in operation" is intended to mean the device during use or application of the device on, to, or near the subject to directly stimulate the vagus nerve to treat inflammatory disorders.

In a further aspect, the methods described relate to the use of a device in the manufacture of a therapeutic article for treating inflammatory disorders in a subject, wherein the device is used solely to stimulate the vagus nerve for the purpose of treating inflammatory disorders. The term "solely" includes the use of the device to selectively treat inflammatory disorders where other diseases or conditions could potentially be treated by stimulation of the vagus nerve.

In some variations, only inflammatory disorders are treated or affected by the direct stimulation of the vagus nerve by the device. In one embodiment, the device may be adapted specifically to treat only inflammatory disorders by direct stimulation of the vagus nerve.

The condition can be one where the inflammatory cytokine cascade causes a systemic reaction, such as with septic shock. Alternatively, the condition can be mediated by a localized inflammatory cytokine cascade, as in rheumatoid arthritis.

Non-limiting examples of conditions which can be usefully treated using these methods include ileus, appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, herpes virus infection disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease.

In another embodiment, the examples of conditions which can be usefully treated include appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, herpes virus infection disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease.

In more preferred embodiments, the condition is ileus, appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In more preferred embodiments, the condition is endotoxic shock.

In another embodiment, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease.

In another preferred embodiment, the conditions are ileus, sepsis, endotoxic shock, allograft rejection, rheumatoid arthritis, adult respiratory distress syndrome, asthma, systemic lupus erythematosis, pancreatitis, peritonitis, burns, myocardial ischemia, allograft rejection, graft-versus-host disease, congestive heart failure, organ ischemia, reperfusion injury, cachexia and cystic fibrosis.

In another embodiment, the conditions are sepsis, endotoxic shock, allograft rejection, rheumatoid arthritis, adult respiratory distress syndrome, asthma, systemic lupus erythematosis, pancreatitis, peritonitis, burns, myocardial ischemia, allograft rejection, graft-versus-host disease, congestive heart failure, organ ischemia, reperfusion injury, cachexia and cystic fibrosis.

In another preferred embodiment, the conditions are ileus, appendicitis, ulcerative colitis, Crohn's disease, allergy, reperfusion injury, systemic lupus erythematosus, hepatitis, Behcet's syndrome, multiple sclerosis and atherosclerosis.

In another embodiment, the conditions are appendicitis, ulcerative colitis, Crohn's disease, allergy, reperfusion injury, systemic lupus erythematosus, hepatitis, Behcet's syndrome, multiple sclerosis and atherosclerosis.

In another embodiment, the conditions are ileus, endotoxic shock and sepsis. In another embodiment, the conditions are endotoxic shock and sepsis.

Also described herein is the use of an electrical signal generator for construction of a medical device for treating a subject suffering from, or at risk for ileus. In yet another embodiment, an electrical signal generator may be used for construction of a medical device for treating a subject suffering from, or at risk for post-operative ileus. The device comprises an electrode assembly for delivering an electrical signal to the vagus nerve of the subject; and a controller controlling the electrical signal by limiting the signal voltage to a range from 0.01 Volt to 1 Volt. Preferably, the controller is limiting the signal voltage to a range from 0.01 Volt to 0.05 Volt. In another embodiment, the controller is limiting pulse width to a range from 0.1 ms to 5 ms; signal frequency to a range from 0.1 Hz to 30 Hz; and signal on-time to a range from 1 second to 120 seconds. In yet another embodiment, the controller is limiting signal voltage to a range from 0.01 Volt to 0.05 Volt; pulse width to a range from 0.1 ms to 0.5 ms; signal frequency to a range from 10 Hz to 30 Hz; and signal on-time to a range from 20 seconds to 40 seconds.

In another embodiment, an electrical signal generator may be used for construction of a medical device for treating a subject suffering from, or at risk for ileus. The device comprises an electrode assembly for delivering an electrical signal to the vagus nerve of the subject; and a controller controlling the electrical signal by limiting the signal voltage to a range from 0.01 Volt to 1 Volt, pulse width to a range from 0.1 ms to 5 ms; signal frequency to a range from 0.1 Hz to 30 Hz; signal on-time to a range from 1 second to 120 seconds; and signal off-time to a range over 2 hours.

Preferably, the controller limits the signal off-time to a range from 2 hours to 48 hours, and more preferably to a range of 16 hours to 30 hours. In another embodiment, the device, in operation, directly stimulates the vagus nerve to treat ileus. In another embodiment, the device is used solely to stimulate the vagus nerve for the purpose of treating ileus.

The methods and systems described above are illustrated by the following examples which are not intended to be limiting in any way.

EXEMPLIFICATION

Example 1

Electrical Vagus Nerve Stimulation Using Decreased Stimulation Intensities and Durations are Sufficient for Activation of the Cholinergic Anti-Inflammatory Pathway To determine whether decreased stimulation parameters could achieve anti-inflammatory effects, intact vagus nerves were electrically stimulated at progressively lower stimulation intensities and durations in the setting of lethal endotoxemia. Male 8- to 12-week-old BALB/c mice (25-30 g; Taconic) were housed at 25° C. on a 12 hour light/dark cycle. Animals were allowed to acclimate to the facility for at least 7 days prior to experimental manipulation. Standard mouse chow and water were freely available. All animal experiments were performed in accordance with the National Institutes of Health (NIH) Guidelines under protocols approved by the Institutional Animal Care and Use Committee of the North Shore-Long Island Jewish Research Institute.

Mice were anesthetized with isoflurane (1.5-2.0%) and placed supine on the operating table. A ventral cervical midline incision was used to expose and isolate the left cervical vagus nerve. For electrical stimulation, the intact vagus nerve was placed across bipolar platinum electrodes (Plastics One) connected to a stimulation module (STM100C, Biopac Systems) and controlled by an acquisition system (MP150, Biopac Systems). Electrical stimulation parameters were programmed using AcqKnowledge software (Biopac Systems). Stimulation parameters included (100 mA, 2 ms, 5 Hz) for 20 min (10 min before LPS administration and 10 min after), (100 mA, 2 ms, 5 Hz) for 2 min (1 min before LPS administration and 1 min after), (100 mA, 2 ms, 5 Hz) for 30 sec (5 min after LPS administration), and (1 mA, 0.5 ms, 30 Hz) for 30 sec (5 min after LPS administration). Sham operated electrical VNS mice underwent cervical incision followed by dissection of the underlying submandibular salivary glands only. The vagus nerve was neither exposed nor isolated.

Mice were injected with endotoxin (*Escherichia coli* LPS 0111:B4; Sigma) that was dissolved in sterile, pyrogen-free saline at stock concentrations of 1 mg/ml. LPS solutions were sonicated for 30 min immediately before use for each experiment. Mice received an $LD_{50}$ dose of LPS (7.5 mg/kg, i.p.). Blood was collected 2 h after LPS administration, allowed to clot for 2 h at room temperature, and then centrifuged for 15 min at 2,000.times.g. Serum samples were stored at −20.degree.C. before analysis. TNF concentrations in mouse serum were measured by ELISA (R & D Systems).

Figure 5:
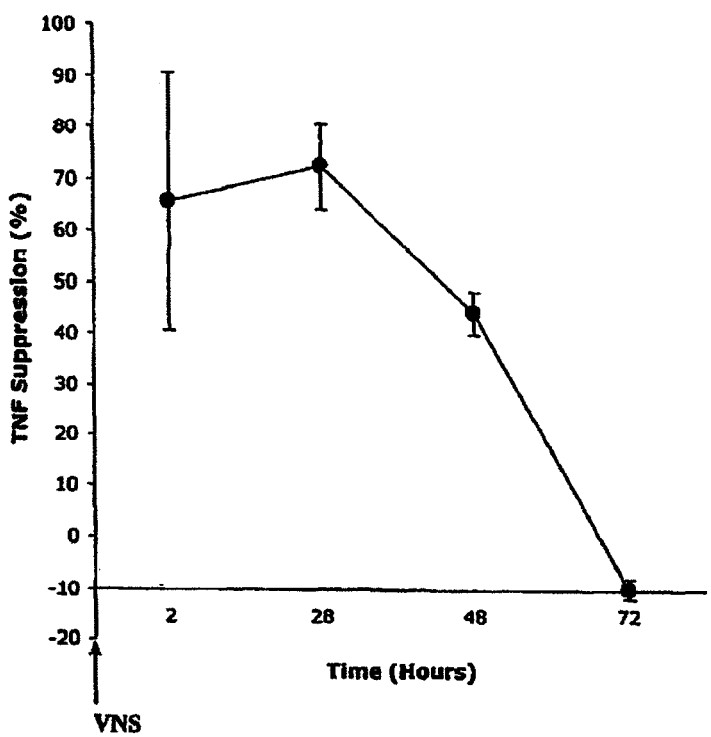
FIG. 5 is a plot showing the effect of electrical VNS on TNF production in LPS-challenged mice. Vertical axis indicates percent suppression of TNF, horizontal axis indicates hours elapsed between the VNS stimulation and LPS challenge. The deviation of TNF suppression substantially exceeds the period of applied VNS.

As shown in FIG. 5, all four stimulation parameters were sufficient for TNF suppression. The control mice group who received LPS followed by sham VNS had a mean serum TNF level of 2755.+−.424 pg/ml. Serum TNF levels in the electrical VNS groups were as follows; 20 min (712.+−.128 pg/ml, 25.8% of control, p=0.02), 2 min (688.+−.114 pg/ml, 25.0% of control, p=0.02), 30 sec at 100 mA (821.+−.378 pg/ml, 29.8% of control, p=0.46), and 30 sec at 1 mA (767.+−.144 pg/ml, 27.8% of control, p=0.03). The 30 sec 1 mA group corresponds to a clinically approved stimulation protocol (REF).

These results indicate that cholinergic anti-inflammatory pathway activation is responsive to physiologic, clinically well-tolerated electrical stimulation parameters. Additionally, the application of supraphysiologic current doses or prolonged stimulation durations does not provide any additional benefits in terms of reduced pro-inflammatory cytokine production.

Example 2

The Effective Duration of Action of Electrical Vagus Nerve Stimulation-Mediated TNF Suppression is Between Two and Three Days To determine how long the anti-inflammatory effects of vagus nerve stimulation last after the completion of stimulation, mice underwent electrical stimulation for 30 sec (1 mA, 0.5 ms, 30 Hz), and were allowed to recover for defined time periods prior to LPS administration. Control mice underwent sham surgery at time 0 and were challenged with LPS at the identical time periods as stimulated mice. Results for the four experimental groups are depicted in FIG. 5. Waiting for two hours between VNS and subsequent lipopolysaccharide (LPS) administration resulted in a 71% suppression of TNF (control=1606.+−.326 pg/ml vs. VNS=474.+−.157 pg/ml, p=0.01). Waiting for one day between VNS and LPS administration resulted in a 72% suppression of TNF (control=2813.+−.503 pg/ml vs. VNS=783.+−.87 pg/ml, p=0.004). Waiting two days between VNS and LPS resulted in a 44% suppression of TNF (control=1590.+−.351 pg/ml vs. VNS=892.+−.85 pg/ml, p=0.09). Finally, waiting for three days resulted in no TNF suppression (control=1253.+−.202 pg/ml vs. VNS=1393.+−.263 pg/ml, p=0.7). Animals were euthanized two hours after LPS administration.

These results indicate that the cholinergic anti-inflammatory pathway's effects are very long lasting, persisting for at least two days after stimulation. Furthermore, there was no significant difference in the anti-inflammatory effects between the two hour delay as opposed to a one day delay prior to LPS challenge. Finally, the data indicate that the anti-inflammatory effects of vagus nerve stimulation in this model had dissipated by three days after stimulation.

Example 3

Electrical Vagus Nerve Stimulation Improves Severity of Arthritis in a Rat Model of Collagen-Induced Arthritis To determine if vagus nerve stimulation could delay the onset or ameliorate the severity of arthritis in a rat collagen-induced arthritis model, rats received repeated vagus nerve stimulation via implanted electrodes for several days after collagen immunization and were scored for arthritis severity.

Purified Rat Type II Collagen (CII) (Chondrex, Redmond, Wash., USA) was dissolved in 0.01M acetic acid. Equal volumes of collagen solution and incomplete Freund's adjuvant (IFA; Difco Laboratories, Detroit, Mich.) were emulsified at 4.degree.C. so that 200 ul of emulsion contains 150 ug of rat CII (Akerlund et al, Clinical & Experimental Immunology 1999 115: 32-41; Kokkola R et al., Arthritis Rheum. 2003 48:2052-8). Rats were immunized intradermally at the base of the tail with a volume of 200 ul per animal. A chronic, destructive arthritis developed with a mean onset of 14 days after immunization.

A previously described, arthritis clinical scoring system was utilized (Kokkola R et al., Arthritis Rheum 2003. 48(7): 2052-2058). This scoring system has proven reliable and highly discriminative for therapeutic studies (Akerlund et al, Clin Exp Immunol 1999, 115:32-41). Rats were observed daily for clinical signs of arthritis, including erythema and swelling of the joints. The interphalangeal joints of the digits, the metacarpophalangeal joint and wrist in the forepaw, and the metatarsophalangeal joint and ankle joint in the hind paw are each considered as one category of joint. Each paw was scored on a scale of 0-4 as follows: 0=unaffected, 1=1 type of joint affected, 2=2 types of joints affected, 3=3 types of joints affected, 4=3 types of joints affected and maximal erythema and swelling. An arthritis index was calculated for each rat and expressed as the cumulative score for all paws, with a maximum possible score of 16. Two independent observers performed all arthritis evaluations. The observers were additionally blinded to the identity of the animals.

Electrical vagus nerve stimulation was started on the 13th day post collagen immunization day (PCID). VNS rats were stimulated for 10 min once a day (5 V, 1-2 mA; 0.5-millisecond pulse; 30 Hz; 10 min on-time of alternating 30 seconds "on" and 300 seconds "off") through day 20 (day 16 was skipped). These stimuli were generated using the STMI-SOC stimulation adapter, STM100C stimulator module, and MP150 Data Acquisition System, all from Biopac Systems, Inc. Where indicated, all animals were anesthetized using isoflurane inhalation gas (2-4%). During surgical procedures, animals were placed on a maintenance anesthesia dose via a mask delivery system. Following isoflurane anesthesia induction, animal were placed in supine position, and a 2 cm ventral midline cervical incision was made between the mandible and sternum. The subcutaneous tissue was dissected and retracted laterally. The mandible salivary glands were bluntly separated and retracted laterally. The left vagus nerve was isolated between the sternomastoid and sternohyoid muscles, dissected free from the neighboring carotid artery, and controlled with a 4-0 silk suture. A Teflon-coated silver electrode 0.003 inch in diameter was secured to the vagus nerve by multiple 360 degree circular wrappings around the nerve. The Teflon only was stripped from the ends of the wire to minimize electrical stimulation of the surrounding cervical muscles. The silver wire ends then were tunneled subcutaneously around the left neck to the dorsal cervical midline. At this point, they were exited through the skin and be attached to stimulating wires traveling through the tether apparatus.

Figure 6:
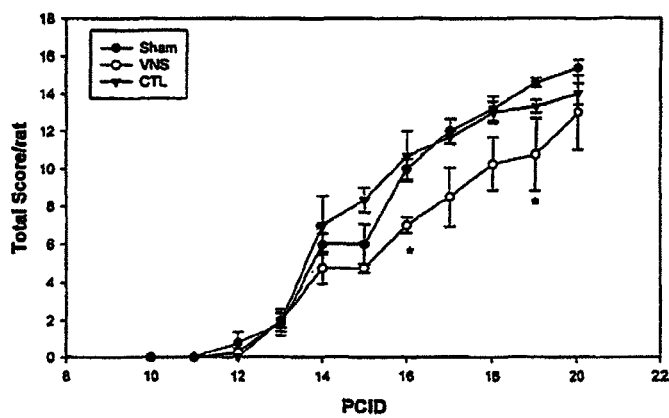
FIG. 6 is a plot that shows an arthritis score in rats as a function of a number of days post collagen immunization to induced arthritis (PCID). VNS stimulation started on day 13 and continued until day 20. The VNS stimulation inhibited the development of PCID.

As shown in FIG. 6, repeated electrical stimulation of the vagus nerve resulted in decreased clinical signs of arthritis (as measured by erythema and swelling of the joints) as compared with control and sham animals (stimulated rats: N=4; sham: N=5; control: N=3.) On day 16, the arthritis score in rats receiving vagus nerve stimulation was significantly less than that in control and sham animals (p<0.05). On day 19, the arthritis score in rats receiving vagus nerve stimulation was significantly less than that in sham treated animals (p<0.05). These results indicate that repeated vagus nerve stimulation is effective at lessening arthritis severity in collagen-induced arthritis.

Example 4

Mouse Model for Electrical Stimulation with Endotoxemia

Animals. Male 8- to 12-wk-old BALB/c mice (25-30 g; Taconic) were housed in groups at 25° C. on a 12-hr light/dark cycle. Animals were acclimated to our facility for 7 or more days. All animal experiments were performed in accordance with the National Institutes of Health Guidelines under protocols approved by the Institutional Animal Care and Use Committee of the Feinstein Institute for Medical Research. Animals received different treatments as described subsequently. The allocation of animals to the different treatment groups (five to eight animals per group) was performed randomly. The different number of animals per experimental groups is a result of multiple experiments or deaths that occurred before experimental end points.

Endotoxemia. Mice were injected intraperitoneally with lipopolysaccharide (LPS; *Escherichia coli* 0111:B4; Sigma) dissolved in sterile, pyrogen-free saline that was sonicated for 30 mins immediately before use. Two hours after injection, blood was collected, allowed to clot for 2 hrs at room temperature, and then centrifuged at room temperature for 15 mins at 2000×g. Serum samples were stored at −20° C. before analysis. Enzyme-linked immunosorbent assay was used to measure tumor necrosis factor (TNF) concentrations according to the manufacturer's instructions (R&D Systems, Minneapolis, Minn.).

Electrical Vagus Nerve Stimulation. Mice were anesthetized by isoflurane (1.5% to 2.5%) using a cone mask. A midline cervical incision was made to expose the left vagus, which was suspended across bipolar platinum electrodes (Plastics One) connected to a stimulation module (STM100C, Biopac Systems) and controlled by an acquisition system (MP150, Biopac Systems). Electrical stimulation variables were programmed using AcqKnowledge software (Biopac Systems) and included 1 V, 2 milliseconds, 5 Hz for 20 mins (10 mins before LPS and 10 mins after); 1 V, 2 milliseconds, 5 Hz for 2 mins (1 min before LPS and 1 min after); 1 V, 2 milliseconds, 5 Hz for 30 seconds (5 mins after LPS); and 1 V, 0.5 milliseconds, 30 Hz for 30 seconds (5 mins after LPS). Sham-operated mice underwent subcutaneous tissue dissection without exposure of the vagus nerve.

Subdiaphragmatic Vagotomy. A midline laparotomy incision was made, and the intestines and stomach were retracted to expose the distal esophagus. The ventral vagal branch was identified and divided using sharp dissection. The esophagus was encircled and rotated to expose and divide the dorsal vagal branch. The incision was closed using 6-0 polypropylene sutures. Animals received 1 mL of 0.9% normal saline subcutaneously after surgery. Mice recovered for 7 days before further experimentation.

Heart Rate Measurement. Two unipolar electrodes were placed onto the anterior chest wall of anesthetized mice and attached to an amplifier (ECG100C) and processing unit (MP150). The electrocardiogram was processed offline using AcqKnowledge software. Baseline electrocardiograms were recorded for 5 mins. Experimental groups included neck dissection (sham surgery), vagus nerve dissection, transcutaneous vagus nerve stimulation, or escalating doses of electrical vagus nerve stimulation (1 V, 5 Hz, 2 milliseconds; 5 V, 5 Hz, 2 milliseconds; 5 V, 30 Hz, 0.5 milliseconds). Electrocardiograms were recorded and mean heart rates were compared with baseline values.

Generation of primary Human Macrophages. Peripheral blood mononuclear cells were isolated from the blood of normal volunteers (Long Island Blood Services, Melville, N.Y.) over a Ficoll-Hypaque (Pharmacia Biotech, Uppsala, Sweden) density gradient. Monocytes were isolated by adherence. Macrophages were generated with 2 ng/mL human MCSF for 5 days in RPMI 1640 medium (Life Technologies, Grand Island, N.Y.) supplemented with 10% human serum, penicillin (100 units/mL, Life Technologies), streptomycin (100 µg/mL, Life Technologies), and glutamine (2 mM, Life Technologies). To determine the effect of acetylcholine on endotoxin response, the cells were treated with acetylcholine chloride (10 µM, Sigma) in the presence of acetylcholine esterase inhibitor (pyridostigmine bromide, 1 mM) in Opti-MEM I media (GibcoBRL) for 1 hr. The cells were washed once with 1× phosphate buffered saline (Fisher) and suspended in complete medium supplemented with human MCSF. The macrophages received 4 hrs of LPS (10 ng/mL, *E. coli* 0111:B4, Sigma) stimulation in Opti-MEM I, beginning 2, 24, 48, and 72 hrs after acetylcholine exposure. Supernatants were collected and TNF was analyzed by enzyme-linked immunosorbent assay.

Cecal Ligation and Puncture. CLP was performed on BALB/c mice as described previously (19). Animals received antibiotic (Primaxin; 0.5 mg/kg, subcutaneously) and 0.9% normal saline (20 mL/kg body weight, subcutaneously) immediately after surgery. Mice underwent transcutaneous vagus nerve stimulation or sham stimulation beginning 24 hrs after surgery and thereafter twice a day for 2 days. Serum HMGB1 levels were determined 44 hrs after surgery by Western blot as described previously (14, 17). HMGB1 concentrations were calculated against standard curves generated using purified recombinant HMGB1 (14, 17). Serum interleukin-10 levels were measured using Cytometric Bead Array (Becton Dickinson) according to the manufacturer's instructions.

Clinical Sickness Score. Animals were assessed 44 hrs after CLP. The sickness score is composed of four clinical signs, including diarrhea, piloerection, spontaneous eye opening, and activity level. The presence of each component is worth either 1 point (diarrhea, piloerection) or 1-2 points (eye opening, activity level), depending on severity. A maximum score of 6 denotes a moribund animal with 100% mortality within 24 hrs. A score of 0 denotes a healthy, nonseptic animal.

Statistics. All data are expressed as mean±SEM. One-way analysis of variance followed by the Bonferroni correction was used to compare mean values between three groups. The two-tailed Student's t-test was used to compare mean values between two groups. Differences in survival were determined using the log-rank test. P values<0.05 were considered significant.

Results

Figure 7:
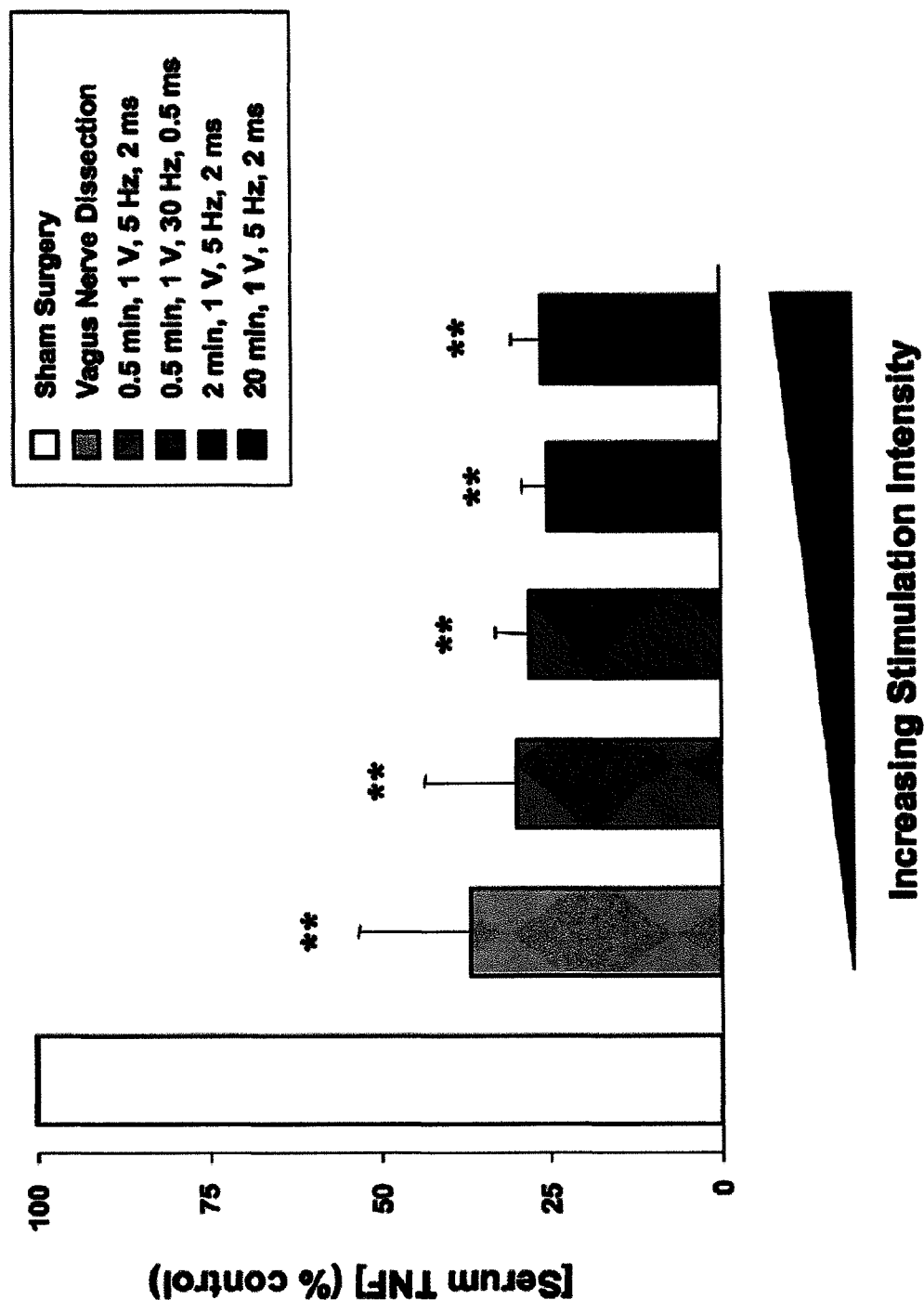
FIG. 7 illustrates the effect of direct stimulation of the vagus nerve, showing attenuation of serum TNF concentrations. BALB/c mice received LPS (7.5 mg/kg, intraperitoneally) 5 minutes before either surgical dissection alone or increasing intensities of electrical vagus nerve stimulation. Blood was collected 2 hrs after endotoxin administration. Data are presented as mean±SEM (n=6-8 per group; **p<0.05).

Electrical stimulation was chronically administered to mice using implanted wire electrodes. Increasing doses of electricity following surgical isolation of the vagus nerve did not suppress TNF concentrations further, as illustrated in FIG. 7.

Anti-Inflammatory and Cardioinhibitory Effects of Vagus Nerve Stimulation are Dissociable.

Figure 8:
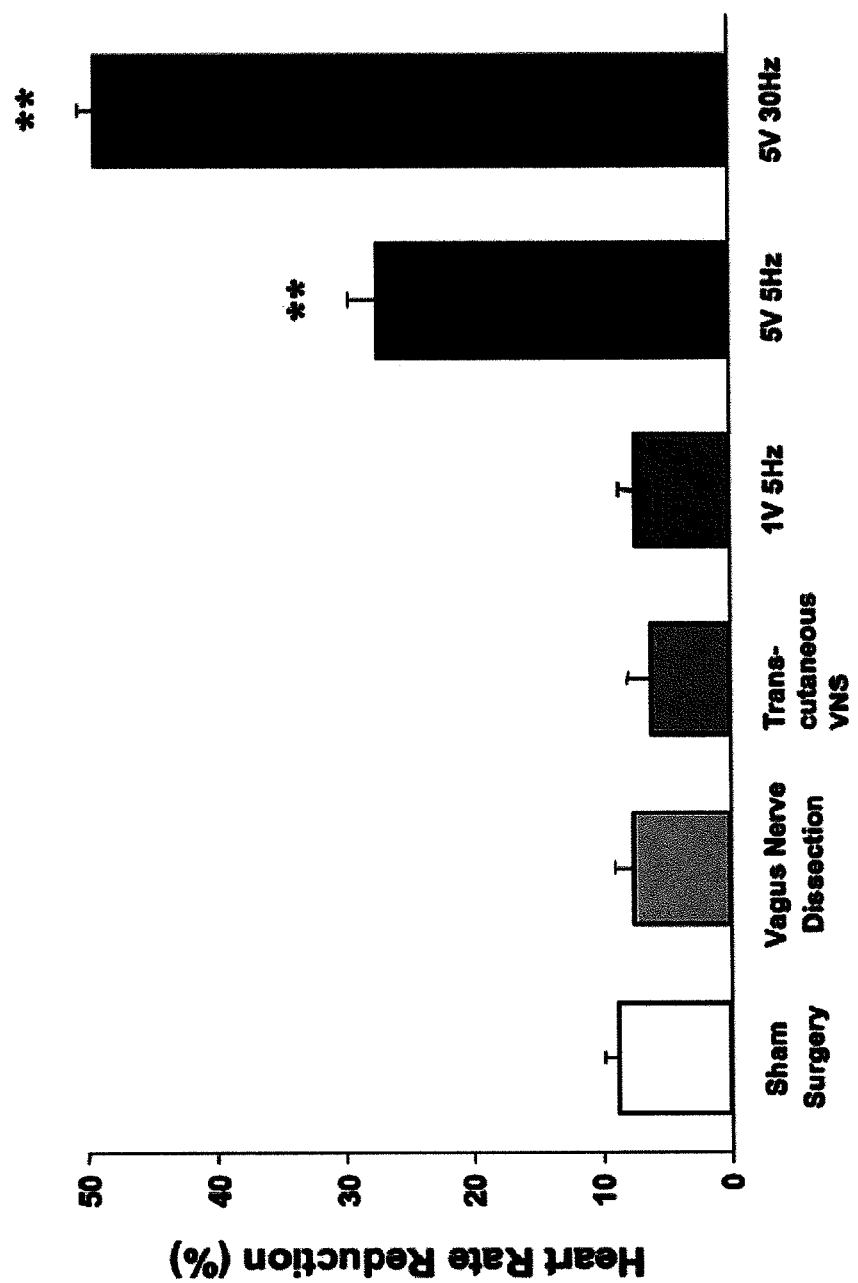
FIG. 8 illustrates the anti-inflammatory and cardioinhibitory effects of vagus nerve stimulation (VNS), showing that the two are dissociable. Electrocardiograms were recorded for 5 minutes from BALB/c mice subjected to neck dissection (sham surgery), vagus nerve dissection, transcutaneous vagus nerve stimulation (300 seconds, 2 Hz) or increasing intensities of electrical vagus nerve stimulation (1 V, 5 Hz, 2 milliseconds; 5 V, 5 Hz, 2 milliseconds; 5 V, 30 Hz, 2 milliseconds). Changes in mean heart rate were compared with baseline. Data are presented as mean±SEM (n=6-8 per group; **p<0.05).

The vagus nerve modulates numerous autonomic functions (20). To address the specificity of vagal anti-inflammatory signaling, we measured heart rate in animals receiving vagus nerve dissection, transcutaneous vagus nerve stimulation, or electrical vagus nerve stimulation (1 V, 5 Hz, 2 milliseconds) and observed no significant effects on heart rate with any of these treatments, as shown in FIG. 8. To ensure that vagus nerve stimulation can elicit "classic" cardioinhibitory effects, we delivered more intense stimuli (5 V, 5 Hz, 2 milliseconds; or 5 V, 30 Hz, 2 milliseconds) and observed a 27.3%±2.3% and 49.1% 2.1% decrease in heart rate, respectively (p<0.05).

Effective Duration of Action of Vagus Nerve Stimulation and Cholinergic Agonists is Between 48 and 72 hrs.

Figure 9A:
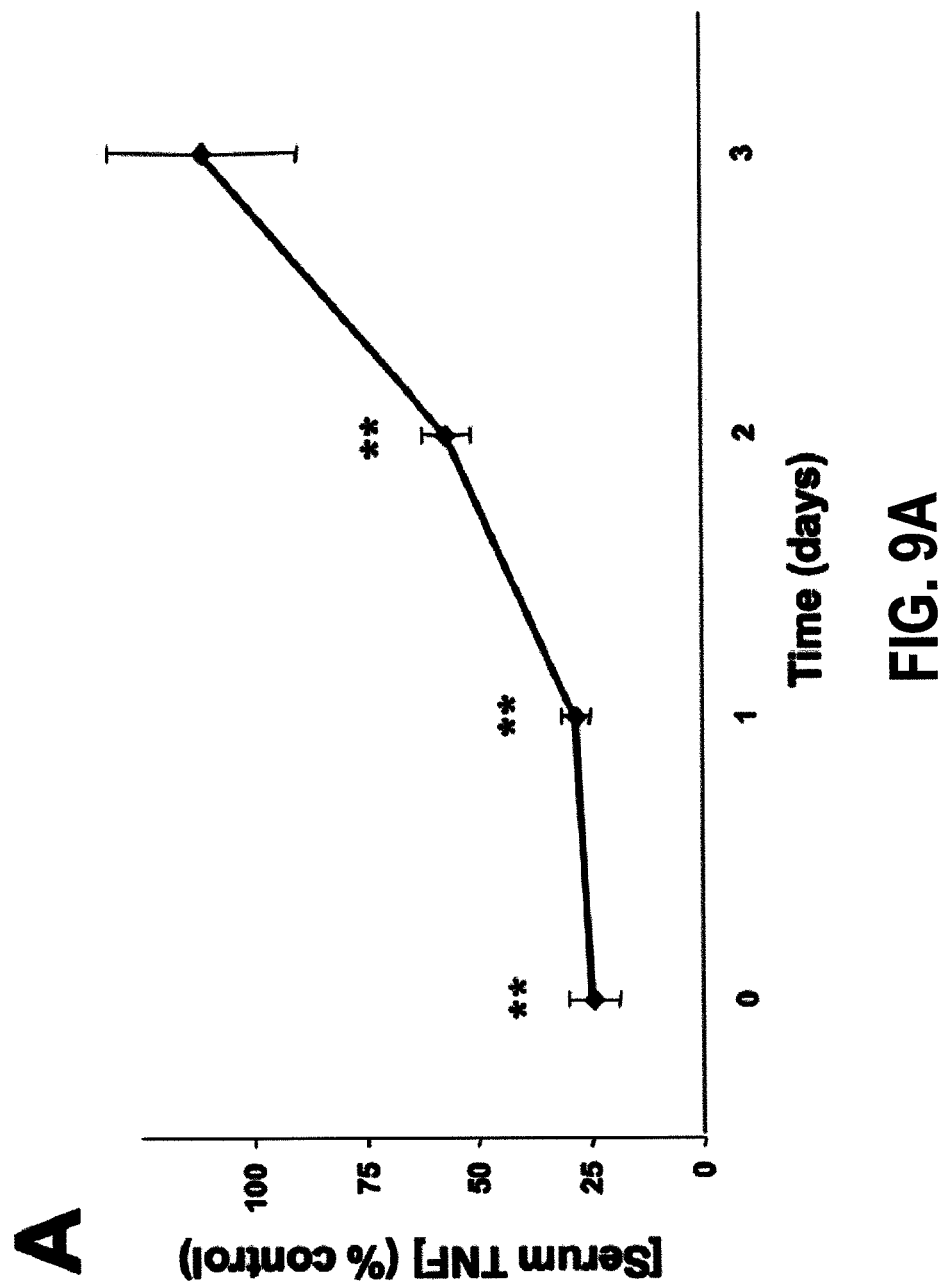
FIG. 9A shows that the effective duration of action of vagus nerve stimulation is between 48 and 72 hrs after VNS. BALB/c mice were subjected to electrical vagus nerve stimulation (30 seconds, 1 V, 30 Hz, 0.5 milliseconds) or neck dissection alone (control) on day 0 and were allowed to recover for 2, 24, 48, or 72 hrs before LPS challenge (7.5 mg/kg; intraperitoneally). Blood was collected 2 hrs after LPS administration for tumor necrosis factor (TNF) analysis. Data are presented as mean±SEM (n=6-8 per group; **p<0.05).

To study the effective duration of action of vagal anti-inflammatory signaling, we gave the mice electrical vagus nerve stimulation or sham stimulation, followed by defined recovery periods before endotoxin challenge. We observed that vagus nerve stimulation significantly reduced serum TNF concentrations when LPS was administered 48 hrs following treatment, but not after 72 hrs. This is illustrated in FIG. 9A.

Figure 9B:
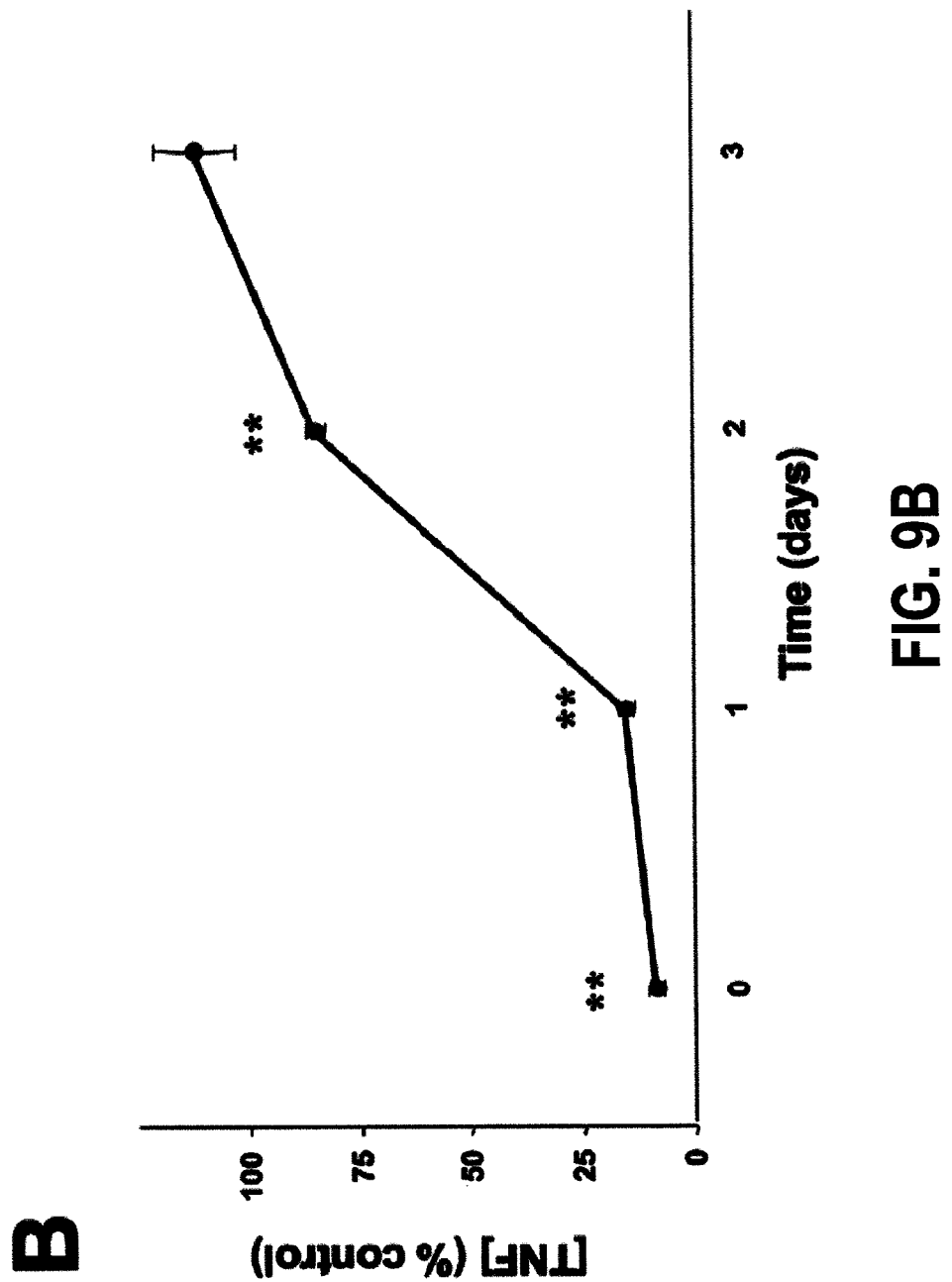
FIG. 9B illustrates the inhibition of TNF release from macrophages for 48 to 72 hrs by acetylcholine. Primary human macrophages were treated with acetylcholine (10 μM) and pyridostigmine bromide (1 mM) for 1 hr, were transferred to fresh media, and then received 4 hrs of LPS (10 ng/mL) stimulation beginning 2, 24, 48, or 72 hrs after acetylcholine exposure. Supernatants were collected and TNF was analyzed by enzyme-linked immunosorbent assay. Data are presented as mean±SEM of two separate experiments (**p<0.05).

To elucidate a mechanism for this relatively long neural duration of action of the anti-inflammatory effect of vagus nerve stimulation, we next examined the TNF-suppressive effects of cholinergic agonists on endotoxin-stimulated primary human macrophages. Macrophage cell cultures were stimulated with acetylcholine together with the acetylcholinesterase inhibitor pyridostigmine for 1 hr, and then cells were washed and suspended in fresh media. Macrophages were stimulated with endotoxin 24, 48, or 72 hrs postexposure to cholinergic treatment. We observed that cholinergic treatment significantly attenuated TNF release for 48 hrs, but not 72 hrs after exposure, as shown in FIG. 9B. These results suggest that cholinergic signaling in macrophages may contribute to the long-lived anti-inflammatory effects of vagus nerve stimulation. For example, refer to FIG. 9A.

Vagus Nerve Stimulation Fails to Induce Hyperglycemia or Cell Death.

Figure 10B:
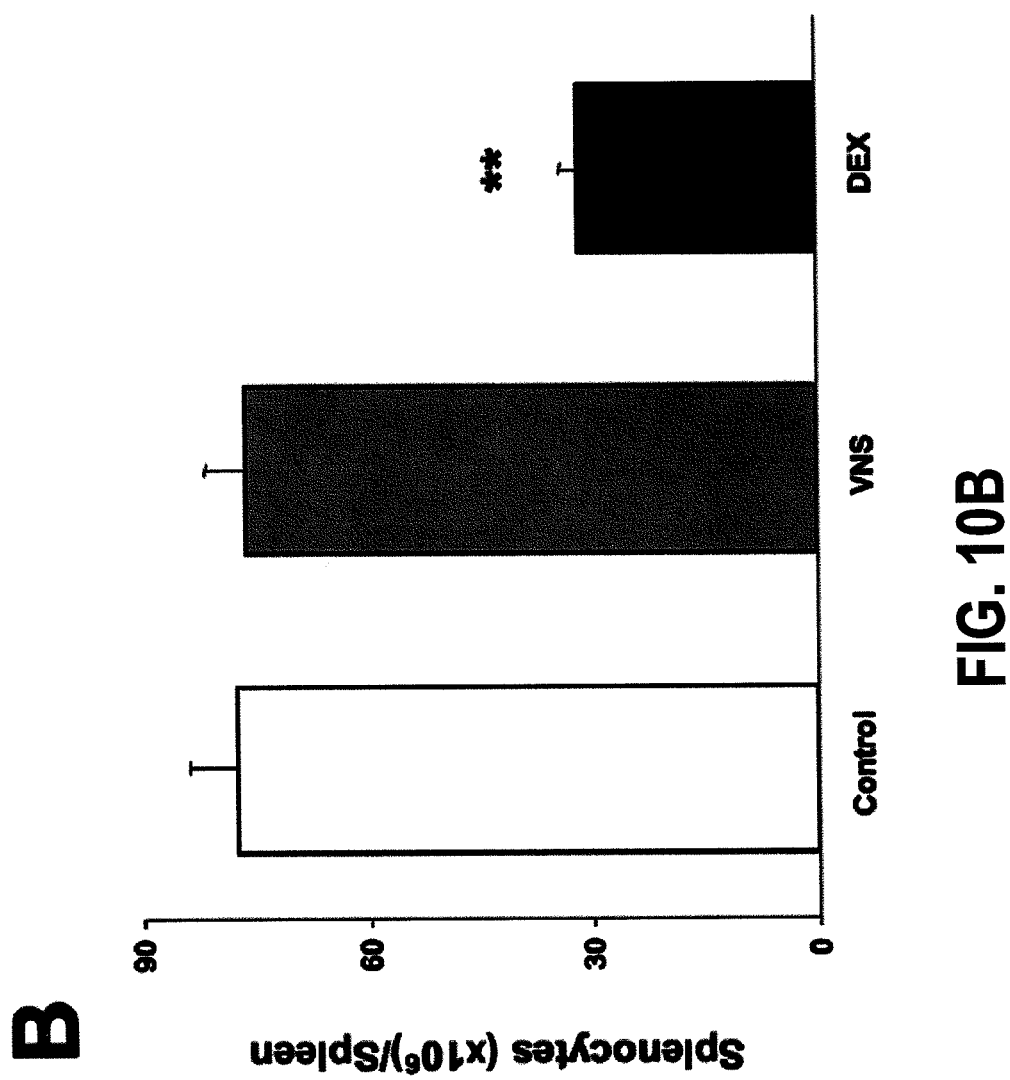
FIG. 10B illustrates the effects of vagus nerve stimulation versus dexamethasone (DEX) on splenocyte viability. Mice were subjected to electrical vagus nerve stimulation (30 seconds, 1 V, 5 Hz, 2 milliseconds) or dexamethasone (25 mg/kg, intraperitoneally) 24 hrs before LPS administration (7.5 mg/kg, intraperitoneally). Animals were euthanized 2 hrs after LPS, spleens were harvested, and viable splenocytes were measured. Data are presented as mean±SEM (n=6 per group; **p<0.05).

The systemic side effect profile of vagus nerve stimulation is currently unknown. We compared vagus nerve stimulation to administration of glucocorticoids, a previously known approach in the treatment of inflammatory diseases, by measuring serum glucose concentrations and splenocyte viability in endotoxemic mice, as shown in FIG. 10A. We observed that vagus nerve stimulation significantly lowered serum glucose concentrations during lethal endotoxemia. Administration of dexamethasone significantly reduced viable splenocyte counts, while vagus nerve stimulation preserved splenocyte viability, as illustrated in FIG. 10B.

As discussed above, the nervous system regulates proinflammatory cytokine production through an α7nAChR-dependent, vagus nerve mediated pathway to the spleen. Electrical vagus nerve stimulation inhibits pro-inflammatory cytokine production and prevents lethal shock in acute models of systemic inflammation.

HMGB1 is a necessary and sufficient mediator of lethal organ damage in murine CLP sepsis. Systemic HMGB1 concentrations are significantly elevated in this model, while neutralizing antibodies directed against HMGB1 significantly reduce organ damage and improve survival. Pharmacologic agents that reduce circulating HMGB1 concentrations, such as ethyl pyruvate and nicotine, also provide significant protection against polymicrobial sepsis lethality. In addition, infusion of HMGB1 to rodents causes organ damage and epithelial barrier failure. On the contrary, the pluripotent, pro-inflammatory cytokine TNF has not been found to be a critical mediator of organ damage and lethality in this model. Vagus nerve stimulation significantly reduces systemic HMGB1 concentrations in septic mice and thereby protects against the development of lethal organ damage.

Pharmacologic α7nAChR agonists, such as nicotine, can mimic the effects of vagus nerve stimulation but may be complicated by poor specificity and systemic toxicity. We show here that vagal anti-inflammatory signaling is specific and dissociable from heart rate regulation, suggesting that it may be a less toxic route for activating the cholinergic anti-inflammatory pathway. Interestingly, the vagus nerve is comprised of A, B, and C fiber subtypes, and the B and C subtypes have been implicated in mammalian heart rate regulation. The dissociability and lower activation threshold of vagal anti-inflammatory signaling allow us to hypothesize that the A fibers, which have the lowest activation threshold and do not appear to participate in heart rate regulation, may fulfill the role of cholinergic anti-inflammatory fibers.

We also showed that vagus nerve stimulation suppressed serum TNF levels even when applied 48 hrs before LPS administration, which is comparable to the cholinergic suppression of TNF in vitro. Future studies will contribute to revealing detailed mechanisms underlying this long-lasting anti-inflammatory efficacy. Current anti-inflammatory therapies, such as glucocorticoids, are associated with serious side effects, including hyperglycemia and immune cell apoptosis. We found that vagus nerve stimulation does not reduce splenocyte viability, while glucocorticoids significantly deplete viable splenocytes, suggesting that vagus nerve stimulation may be less toxic to the spleen. Vagus nerve stimulation also significantly lowers serum glucose levels during systemic inflammation. Recent studies have demonstrated the adverse effects of hyperglycemia in critically ill patients and the improvement in outcome that results from tighter glycemic control.

The description above may be readily generalized to describe various parameters and effects for vagus nerve stimulation that are new and very unexpected. In particular, the extremely low level of stimulation (both low intensity, and low duty-cycle) have been seen to have a profound—and chronic—effect on the immune response. By low duty-cycle effect, we are referring to the time stimulation is "on" compared to the time stimulation is "off" (e.g., the ratio of "on" to "off"). Thus, the stimulation (and particularly chronic stimulation) described herein is "off" much more that in it is "on". The high efficacy of these low duty-cycle modulation parameters is unexpected, and may have a profound effect on the way that treatment of immune response (humor and/or cellular) are performed. For example, chronic (or long-term) stimulation may be effectively performed without the risk of negative effects associated with known stimulation protocols of the vagus nerve.

Furthermore, the low-intensity (and low duty cycle) situation may be used safely without interfering with other aspects controlled by the vagus nerve. For example, altered heart rate and blood pressure are not seen with the low-intensity, low duty-cycle modality stimulation. Thus, the vagus nerve may be stimulated either mechanically or electrically in a low-intensity and low duty-cycle fashion without desensitizing the vagus nerve or its targets, and without invoking a potentially unwanted physiological effect (e.g., on heart rate, heart tone, blood pressure, gastric processes, or any other effect attributed to vagal nerve stimulation except the targeted immune response).

Finally, the disclosure here may be used to support mechanical stimulation and electrical stimulation modalities. For example, implantable mechanical and implantable electrical stimulators may be used having low-intensity and low duty-cycle stimulation protocols, as described. Stimulation of the vagus nerve may be performed externally or internally.

While the methods, systems and devices described above have been particularly shown and described with references to preferred embodiments thereof, it will be understood by those skilled in the art that various changes in form and details may be made therein without departing from the scope of the invention encompassed by the appended claims.

What is claimed is:

1. A method of treating an inflammation in a patient, the method comprising:
   stimulating, in a patient suffering from inflammation, the patient's vagus nerve with an electrical signal to achieve a therapeutic effect for treating the inflammation, wherein the signal current is from 1 mA to 100 mA, the signal voltage is from 0.01 Volts to 5 Volts, the pulse width is from 0.1 ms to 5 ms, the signal frequency is from 0.1 Hz to 30 Hz, and the signal on-time is from 1 second to 120 seconds, wherein the stimulation is transcutaneous stimulation of the vagus nerve;
   limiting the stimulation of the vagus nerve to a frequency of between 0.1 Hz and 30 Hz; and
   re-stimulating, by transcutaneous stimulation, the patient's vagus nerve after waiting for an off-time of at least 2 hours and prior to dissipation of the therapeutic effect for treating the inflammation, wherein the therapeutic effect persists for at least 2 hours after stimulation has ended.

2. The method of claim 1 wherein the off-time before the vagus nerve is re-stimulated is from 2 hours to 24 hours.

3. The method of claim 1, wherein the off-time before the vagus nerve is re-stimulated is between about 16 and about 30 hours.

4. The method of claim 1, further comprising monitoring the effect of the stimulation on inflammation in the patient.

5. The method of claim 1, further comprising determining the level of a pro-inflammatory cytokine prior to stimulation.

6. The method of claim 1, wherein the signal current is between 1 mA to 5 mA.

7. The method of claim 1, wherein the therapeutic effect is dissipated by 72 hours after stimulation has ended.

8. The method of claim 1, wherein stimulating comprises stimulating in a patient suffering from inflammation due to rheumatoid arthritis.

9. A method of treating inflammation in a patient, the method comprising:
   applying an electrode to a patient suffering from a chronic inflammatory disorder;
   stimulating, by transcutaneous stimulation, in the patient suffering from inflammation the patient's vagus nerve with an electrical signal from the electrode to achieve a therapeutic effect for treating the inflammation, wherein the signal current is from 1 mA to 100 mA, pulse width is from 0.1 ms to 5 ms; signal frequency is from 0.1 Hz to 30 Hz; signal on-time is from 1 second to 120 seconds;
   limiting the stimulation of the vagus nerve to a frequency of between 0.1 Hz and 30 Hz; and
   re-stimulating, by transcutaneous stimulation, the patient's vagus nerve after waiting for an off-time of at least 2 hours and prior to dissipation of the therapeutic effect for treating the inflammation, wherein the therapeutic effect persists for at least 2 hours after stimulation has ended.

10. The method of claim 9, wherein the chronic inflammatory disorder is selected from the group consisting of appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitits, hepatitis, Crohn's disease, enteritis, Whipple's disease, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alvealitis, bronchiolitis, pharyngitis, pleurisy, sinusitis, influenza, respiratory syncytial virus infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease.

11. The method of claim 9 wherein the off-time before the vagus nerve is re-stimulated is from 2 hours to 24 hours.

12. The method of claim 9, wherein the off-time before the vagus nerve is re-stimulated is between about 16 and about 30 hours.

13. The method of claim 9, further comprising monitoring the effect of the stimulation on inflammation in the patient.

14. The method of claim 9, further comprising determining the level of a pro-inflammatory cytokine prior to stimulation.

15. The method of claim 9, wherein the chronic inflammatory disorder is rheumatoid arthritis.

16. A method of treating an inflammation in a patient, the method comprising:
   stimulating, in a patient suffering from inflammation, the patient's vagus nerve by transcutaneous simulation, with an electrical signal to achieve a therapeutic effect for treating the inflammation, wherein the signal current is from 1 mA to 100 mA, the signal voltage is from 0.01 Volts to 5 Volts, the pulse width is from 0.1 ms to 5 ms, the signal frequency is from 0.1 Hz to 30 Hz, and the signal on-time is from 1 second to 120 seconds;
   limiting the stimulation of the vagus nerve to a frequency of between 0.1 Hz and 30 Hz; and
   re-stimulating the patient's vagus nerve by transcutaneous stimulation, after waiting for an off-time of at least 2 hours and prior to dissipation of the therapeutic effect for treating the inflammation, wherein the therapeutic effect persists for at least 2 hours after stimulation has ended, wherein the duration of the signal on-time is less than 1% of the duration of the signal off-time.

17. The method of claim 16, wherein stimulating comprises stimulating in a patient suffering from inflammation due to rheumatoid arthritis.

\* \* \* \* \*